US008685371B2

(12) United States Patent
Brindle et al.

(10) Patent No.: US 8,685,371 B2
(45) Date of Patent: Apr. 1, 2014

(54) AGENTS FOR DETECTING AND IMAGING CELL DEATH

(75) Inventors: Kevin Brindle, Cambridge (GB); Andre Neves, Cambridge (GB); Maaike De Backer, Leiden (NL); Israt Alam, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 435 days.

(21) Appl. No.: 12/989,310

(22) PCT Filed: Apr. 29, 2009

(86) PCT No.: PCT/GB2009/001082
§ 371 (c)(1),
(2), (4) Date: Oct. 22, 2010

(87) PCT Pub. No.: WO2009/133362
PCT Pub. Date: Nov. 5, 2009

(65) Prior Publication Data

US 2011/0038798 A1 Feb. 17, 2011

(30) Foreign Application Priority Data

Apr. 29, 2008 (GB) .................................. 0807831.3

(51) Int. Cl.
*A61K 49/00* (2006.01)

(52) U.S. Cl.
USPC ......... 424/9.1; 424/1.11; 424/1.65; 424/1.69; 424/9.6; 530/300
(58) Field of Classification Search
USPC ........... 424/1.11, 1.65, 1.69, 1.81, 1.85, 1.89, 424/9.1, 9.3, 9.36, 9.4, 9.42, 9.5, 9.6, 9.7, 424/9.8; 514/1, 1.1; 534/7, 10–16; 530/300, 530/324
See application file for complete search history.

(56) References Cited

U.S. PATENT DOCUMENTS 8,506,928 B2 * 8/2013 Ferrara et al. ................ 424/1.69

FOREIGN PATENT DOCUMENTS

| | | |
|---|---|---|
| WO | WO-03/105814 | 12/2003 |
| WO | WO-2006/055855 | 5/2006 |

OTHER PUBLICATIONS

Krishnan et al., "Detection of Cell Death in Tumors by Using MR Imaging and a Gadolinium-based Targeted Contrast Agent," *Radiology*, vol. 246, No. 3, pp. 854-862 (2008).
Neves et al., "A Paramagnetic Nanoprobe to Detect Tumor Cell Death Using Magnetic Resonance Imaging," *Nano Letters*, vol. 7, No. 5., pp. 1419-1423 (2007).
Wang et al., "Imaging paclitaxel (chemotherapy)-induced tumor apoptosis with $^{99m}$Tc C2A, a domain of synaptotagmin I: a preliminary study," *Nuclear Medicine and Biology*, vol. 35, pp. 359-364 (2008).
International Search Report for PCT/GB2009/001082 dated Feb. 3, 2010.
Written Opinion for PCT/GB2009/001082 dated Feb. 3, 2010.
Chae et al., Lipid binding ridge on loops 2 and 3 of the $C_2$A domain of synaptotagmin I as revealed by NMR spectroscopy, J. of Biol. Chemistry, 273(4): 25659-25663 (1998).
Chapman et al., Direct interaction of a $Ca^{2+}$-binding loop of synaptotagmin with lipid bilayers, J. of Biol. Chemistry, 273(22):13995-14001 (1998).
Tian et al., How well is enzyme function conserved as a function of pairwise sequence identity?, J. Mol. Biol., 333: 863-882 (2003).
Zhang et al., Mechanism of phospholipid binding by the $C_2$A-domain of synaptotagmin I, Biochemistry, 37: 12395-12403 (1998).

* cited by examiner

*Primary Examiner* — D L Jones
(74) *Attorney, Agent, or Firm* — Charles E. Lyon; Robert N. Sahr; Choate, Hall & Stewart LLP

(57) ABSTRACT

This invention relates to molecular imaging agents comprising an S78C mutant synaptotagmin I C2A domain. These agents may be useful in detecting or assessing cell death in vitro and in vivo, for example in tumors following cancer treatment.

20 Claims, 18 Drawing Sheets

SEQUENCE LISTING

<160> NUMBER OF SEQ ID NOS: 10

<210> SEQ ID NO 1
<211> LENGTH: 128
<212> TYPE: PRT
<213> ORGANISM: Artificial sequence
<220> FEATURE:
<223> OTHER INFORMATION: Synthetic sequence: Mutated C2A domain of
      synaptotagmin I

| | | | | | | | | | | | | | | |
|---|---|---|---|---|---|---|---|---|---|---|---|---|---|---|
| Glu | Lys | Leu | Gly | Lys | Leu | Gln | Tyr | Ser | Leu | Asp | Tyr | Asp | Phe | Gln | Asn |
| 1 | | | 5 | | | | | 10 | | | | | 15 | | |

Asn Gln Leu Leu Val Gly Ile Ile Gln Ala Ala Glu Leu Pro Ala Leu
        20                  25                  30

Asp Met Gly Gly Thr Ser Asp Pro Tyr Val Lys Val Phe Leu Leu Pro
            35                  40                  45

Asp Lys Lys Lys Lys Phe Glu Thr Lys Val His Arg Lys Thr Leu Asn
 50                  55                  60

Pro Val Phe Asn Glu Gln Phe Thr Phe Lys Val Pro Tyr Cys Glu Leu
65              70                  75                  80

Gly Gly Lys Thr Leu Val Met Ala Val Tyr Asp Phe Asp Arg Phe Ser
                85                  90                  95

Lys His Asp Ile Ile Gly Glu Phe Lys Val Pro Met Asn Thr Val Asp
            100                 105                 110

Phe Gly His Val Thr Glu Glu Trp Arg Asp Leu Gln Ser Ala Glu Lys
        115                 120                 125

<210> SEQ ID NO 2
<211> LENGTH: 384
<212> TYPE: DNA
<213> ORGANISM: Artificial sequence
<220> FEATURE:
<223> OTHER INFORMATION: Synthetic sequence: Mutated C2A domain coding
      sequence

<400> SEQUENCE: 2

```
gagaaactgg gaaagctcca atattcactg gactatgact tccagaataa ccagctgttg    60
gtgggaatca tccaggctgc tgaactgccc gccctggaca tgggggggtac atccgatcca   120 tacgtcaaag tcttcctgct gcctgacaaa aagaagaaat tgagactaa agtccaccgg    180 aaaaccctca atccagtctt caatgaacaa tttactttca aggtaccccta ctgcgaatta   240 ggtggcaaaa ccctggtgat ggctgtgtat gactttgatc gcttctccaa gcacgacatc   300
atcggagagt tcaaagttcc tatgaacacc gtggattttg ccatgtgac cgaggagtgg    360 cgcgatctcc agagcgctga gaaa                                          384
```

<210> SEQ ID NO 3
<211> LENGTH: 5379
<212> TYPE: DNA
<213> ORGANISM: Artificial sequence
<220> FEATURE:
<223> OTHER INFORMATION: Synthetic sequence: pGEX-2T vector with C2A-GST
      fusion insert
<220> FEATURE:
<221> NAME/KEY: misc_feature
<222> LOCATION: (929)..(929)
<223> OTHER INFORMATION: n is a or g or c or t

<400> SEQUENCE: 3

```
acgttatcga ctgcacggtg caccaatgct tctggcgtca ggcagccatc ggaagctgtg    60
gtatggctgt gcaggtcgta aatcactgca taattcgtgt cgctcaaggc gcactcccgt   120
tctggataat gttttttgcg ccgacatcat aacggttctg gcaaatattc tgaaatgagc   180
tgttgacaat taatcatcgg ctcgtataat gtgtggaatt gtgagcggat aacaatttca   240
cacaggaaac agtattcatg tcccctatac taggttattg gaaaattaag ggccttgtgc   300 aaccccactcg acttcttttg gaatatcttg aagaaaaata tgaagagcat ttgtatgagc   360
gcgatgaagg tgataaatgg cgaaacaaaa agtttgaatt gggtttggag tttcccaatc   420
ttccttatta tattgatggt gatgttaaat taacacagtc tatggccatc atacgttata   480
```

```
tagctgacaa gcacaacatg ttgggtggtt gtccaaaaga gcgtgcagag atttcaatgc    540
ttgaaggagc ggttttggat attagatacg gtgtttcgag aattgcatat agtaaagact    600
ttgaaactct caaagttgat tttcttagca agctacctga aatgctgaaa atgttcgaag    660
atcgtttatg tcataaaaca tatttaaatg gtgatcatgt aacccatcct gacttcatgt    720
tgtatgacgc tcttgatgtt gttttataca tggacccaat gtgcctggat gcgttcccaa    780
aattagtttg ttttaaaaaa cgtattgaag ctatcccaca aattgataag tacttgaaat    840
ccagcaagta tatagcatgg cctttgcagg gctggcaagc cacgtttggt ggtggcgacc    900
atcctccaaa atcggatctg gttccgcgng gatccccggg aatttccggt ggtggtggtg    960
gaattctaga ctccatggtg gagaaactgg gaaagctcca atattcactg gactatgact   1020
tccagaataa ccagctgttg gtgggaatca tccaggctgc tgaactgccc gccctggaca   1080 tgggggtac atccgatcca tacgtcaaag tcttcctgct gcctgacaaa agaagaaat    1140 ttgagactaa agtccaccgg aaaaccctca atccagtctt caatgaacaa tttactttca   1200
aggtacccta ctgcgaatta ggtggcaaaa ccctggtgat ggctgtgtat gactttgatc   1260
gcttctccaa gcacgacatc atcggagagt tcaaagttcc tatgaacacc gtggattttg   1320
gccatgtgac cgaggagtgg cgcgatctcc agagcgctga gaaataagct taattcatcg   1380
tgactgactg acgatctgcc tcgcgcgttt cggtgatgac ggtgaaaacc tctgacacat   1440
gcagctcccg gagacggtca gcttgtctt gtaagcggat gccgggagca gacaagcccg   1500
tcagggcgcg tcagcgggtg ttggcgggtg tcggggcgca gccatgaccc agtcacgtag   1560
cgatagcgga gtgtataatt cttgaagacg aaagggcctc gtgatacgcc tatttttata   1620
ggttaatgtc atgataataa tggtttctta gacgtcaggt ggcacttttc ggggaaatgt   1680
gcgcggaacc cctatttgtt tattttttcta aatacattca aatatgtatc cgctcatgag   1740
acaataaccc tgataaatgc ttcaataata ttgaaaaagg aagagtatga gtattcaaca   1800
tttccgtgtc gcccttattc ccttttttgc ggcattttgc cttcctgttt ttgctcaccc   1860
agaaacgctg gtgaaagtaa aagatgctga agatcagttg ggtgcacgag tgggttacat   1920
cgaactggat ctcaacagcg gtaagatcct tgagagtttt cgccccgaag aacgttttcc   1980
aatgatgagc acttttaaag ttctgctatg tggcgcggta ttatcccgtg ttgacgccgg   2040
gcaagagcaa ctcggtcgcc gcatacacta ttctcagaat gacttggttg agtactcacc   2100
agtcacagaa aagcatctta cggatggcat gacagtaaga gaattatgca gtgctgccat   2160
aaccatgagt gataacactg cggccaactt acttctgaca acgatcggag gaccgaagga   2220
gctaaccgct tttttgcaca acatggggga tcatgtaact cgccttgatc gttgggaacc   2280
ggagctgaat gaagccatac caaacgacga gcgtgacacc acgatgcctg cagcaatggc   2340
aacaacgttg cgcaaactat taactggcga actacttact ctagcttccc ggcaacaatt   2400
aatagactgg atggaggcgg ataaagttgc aggaccactt ctgcgctcgg cccttccggc   2460
tggctggttt attgctgata atctggagc cggtgagcgt gggtctcgcg gtatcattgc   2520
agcactgggg ccagatggta agccctcccg tatcgtagtt atctacacga cggggagtca   2580
ggcaactatg gatgaacgaa atagacagat cgctgagata ggtgcctcac tgattaagca   2640
ttggtaactg tcagaccaag tttactcata tactttag attgatttaa aacttcattt   2700
ttaatttaaa aggatctagg tgaagatcct ttttgataat ctcatgacca aaatccctta   2760
acgtgagttt tcgttccact gagcgtcaga ccccgtagaa aagatcaaag gatcttcttg   2820
agatcctttt tttctgcgcg taatctgctg cttgcaaaca aaaaaaccac cgctaccagc   2880
```

```
ggtggtttgt tgccggatc aagagctacc aactctttt ccgaaggtaa ctggcttcag   2940
cagagcgcag ataccaaata ctgtccttct agtgtagccg tagttaggcc accacttcaa   3000
gaactctgta gcaccgccta catacctcgc tctgctaatc ctgttaccag tggctgctgc   3060
cagtggcgat aagtcgtgtc ttaccgggtt ggactcaaga cgatagttac cggataaggc   3120
gcagcggtcg ggctgaacgg ggggttcgtg cacacagccc agcttggagc gaacgaccta   3180
caccgaactg agatacctac agcgtgagct atgagaaagc gccacgcttc ccgaagggag   3240
aaaggcggac aggtatccgg taagcggcag ggtcggaaca ggagagcgca cgagggagct   3300
tccaggggga aacgcctggt atctttatag tcctgtcggg tttcgccacc tctgacttga   3360
gcgtcgattt tgtgatgct cgtcaggggg cggagccta tggaaaaacg ccagcaacgc   3420
ggccttttta cggttcctgg ccttttgctg ccttttgct cacatgttct ttcctgcgtt   3480
atcccctgat tctgtggata accgtattac cgcctttgag tgagctgata ccgctcgccg   3540
cagccgaacg accgagcgca gcgagtcagt gagcgaggaa gcggaagagc gcctgatgcg   3600
gtattttctc cttacgcatc tgtgcggtat ttcacaccgc ataaattccg acaccatcga   3660
atggtgcaaa acctttcgcg gtatggcatg atagcgcccg gaagagagtc aattcagggt   3720
ggtgaatgtg aaaccagtaa cgttatacga tgtcgcagag tatgccggtg tctcttatca   3780
gaccgtttcc cgcgtggtga accaggccag ccacgtttct gcgaaaacgc gggaaaaagt   3840
ggaagcggcg atggcggagc tgaattacat tcccaaccgc gtggcacaac aactggcggg   3900
caaacagtcg ttgctgattg gcgttgccac ctccagtctg gccctgcacg cgccgtcgca   3960
aattgtcgcg gcgattaaat ctcgcgccga tcaactgggt gccagcgtgg tggtgtcgat   4020
ggtagaacga agcggcgtcg aagcctgtaa agcggcggtg cacaatcttc tcgcgcaacg   4080
cgtcagtggg ctgatcatta actatccgct ggatgaccag gatgccattg ctgtggaagc   4140
tgcctgcact aatgttccgg cgttatttct tgatgtctct gaccagacac ccatcaacag   4200
tattattttc tcccatgaag acggtacgcg actgggcgtg gagcatctgg tcgcattggg   4260
tcaccagcaa atcgcgctgt tagcgggccc attaagttct gtctcggcgc gtctgcgtct   4320
ggctggctgg cataaatatc tcactcgcaa tcaaattcag ccgatagcgg aacgggaagg   4380
cgactggagt gccatgtccg gttttcaaca aaccatgcaa atgctgaatg agggcatcgt   4440
tcccactgcg atgctggttg ccaacgatca gatggcgctg ggcgcaatgc gcgccattac   4500
cgagtccggg ctgcgcgttg gtgcggatat ctcggtagtg ggatacgacg ataccgaaga   4560
cagctcatgt tatatcccgc cgttaaccac catcaaacag gattttcgcc tgctgggca   4620 aaccagcgtg gaccgcttgc tgcaactctc tcagggccag gcggtgaagg gcaatcagct   4680 gttgccgtc tcactggtga aagaaaaac caccctggcg cccaatacgc aaaccgcctc   4740 tcccgcgcg ttggccgatt cattaatgca gctggcacga caggtttccc gactggaaag   4800
cgggcagtga gcgcaacgca attaatgtga gttagctcac tcattaggca ccccaggctt   4860
tacactttat gcttccggct cgtatgttgt gtggaattgt gagcggataa caatttcaca   4920
caggaaacag ctatgaccat gattacggat tcactggccg tcgttttaca acgtcgtgac   4980
tgggaaaacc ctggcgttac ccaacttaat cgccttgcag cacatccccc tttcgccagc   5040
tggcgtaata gcgaagaggc ccgcaccgat cgcccttccc aacagttgcg cagcctgaat   5100
ggcgaatggc gctttgcctg gtttccggca ccagaagcgg tgccggaaag ctggctggag   5160
tgcgatcttc ctgaggccga tactgtcgtc gtcccctcaa actggcagat gcacggttac   5220
gatgcgccca tctacaccaa cgtaacctat cccattacgg tcaatccgcc gtttgttccc   5280
```

```
acggagaatc cgacgggttg ttactcgctc acatttaatg ttgatgaaag ctggctacag    5340
gaaggccaga cgcgaattat ttttgatggc gttggaatt                           5379
```

```
<210> SEQ ID NO 4
<211> LENGTH: 10
<212> TYPE: PRT
<213> ORGANISM: Artificial sequence
<220> FEATURE:
<223> OTHER INFORMATION: Synthetic sequence: Purification tag sequence

<400> SEQUENCE: 4

Met Arg Gly Ser His His His His His His
1               5                   10

<210> SEQ ID NO 5
<211> LENGTH: 8
<212> TYPE: PRT
<213> ORGANISM: Artificial sequence
<220> FEATURE:
<223> OTHER INFORMATION: Synthetic sequence: FLAG purification tag
      sequence

<400> SEQUENCE: 5

Asp Tyr Lys Asp Asp Asp Asp Lys
1               5

<210> SEQ ID NO 6
<211> LENGTH: 15
<212> TYPE: PRT
<213> ORGANISM: Artificial sequence
<220> FEATURE:
<223> OTHER INFORMATION: Synthetic sequence: Purification tag sequence

<400> SEQUENCE: 6

Lys Glu Thr Ala Ala Ala Lys Phe Glu Arg Gln His Met Asp Ser
1               5                   10                  15

<210> SEQ ID NO 7
<211> LENGTH: 8
<212> TYPE: PRT
<213> ORGANISM: Artificial sequence
<220> FEATURE:
<223> OTHER INFORMATION: Synthetic sequence: Strept-tag II purification
      tag sequence

<400> SEQUENCE: 7

Trp Ser His Pro Gln Phe Glu Lys
1               5

<210> SEQ ID NO 8
<211> LENGTH: 10
<212> TYPE: PRT
<213> ORGANISM: Artificial sequence
<220> FEATURE:
<223> OTHER INFORMATION: Synthetic sequence: c-myc purification tag
      sequence

<400> SEQUENCE: 8

Glu Gln Lys Leu Ile Ser Glu Glu Asp Leu
1               5                   10

<210> SEQ ID NO 9
<211> LENGTH: 12
<212> TYPE: PRT
<213> ORGANISM: Artificial sequence
<220> FEATURE:
<223> OTHER INFORMATION: Synthetic sequence: Cruz tag 09 sequence
```

```
<400> SEQUENCE: 9

Met Lys Ala Glu Phe Arg Arg Gln Glu Ser Asp Arg
1               5                   10

<210> SEQ ID NO 10
<211> LENGTH: 12
<212> TYPE: PRT
<213> ORGANISM: Artificial sequence
<220> FEATURE:
<223> OTHER INFORMATION: Synthetic sequence: Cruz tag 22 sequence

<400> SEQUENCE: 10

Met Arg Asp Ala Leu Asp Arg Leu Asp Arg Leu Ala
1               5                   10
```

AGENTS FOR DETECTING AND IMAGING CELL DEATH

RELATED APPLICATIONS

This application is a national phase application under 35 U.S.C. 371 of PCT International Application No. PCT/GB2009/001082 (published PCT application no. WO 2009/133362), filed Apr. 29, 2009, the contents of which are hereby incorporated by reference in their entirety for all purposes.

This invention relates to imaging agents for use in molecular imaging and, in particular, for detecting the onset and extent of cell death in vivo.

The speed of onset and extent of cell death in tumours following therapy is considered a good prognostic indicator for treatment outcome. Targeted imaging agents, for example for Magnetic Resonance Imaging (MRI), that are able to detect the onset and extent of cell death in vivo are therefore useful, for example, in assessing the efficacy of cancer treatment. Detection of the onset and extent of cell death in vivo may also be useful in other pathological situations, such as a cardiac infarct, cardiac plaque, inflammation or infection.

Annexin V, which binds to phosphatidylserine (PS) externalised on the surface of dying cells, has been used in imaging agents to detect cell death in vivo. However, annexin V has several limitations which include, large size (36 kDa), a complex GMP production process, and slow renal clearance in vivo, which have limited its clinical use as an imaging agent (Han et al. (2008), *Nat Med* 14(3):343; van de Wiele et al. (2003), *J Clin Oncol* 21:3483; Belhocine et al. (2002), *Clin Cancer Res* 8: 2766.

The C2A domain of synaptotagmin I, which also binds to phosphatidylserine (PS), has been labelled with iron oxide nanoparticles and used to detect cell death in vivo [Zhao M et al. Nat Med. 7(11):1241, 2001]. The utility of this approach, however, was limited, by the relatively large size of these constructs (~25 nm), which restricted both the extravasation of the construct from the vasculature, and also the clearance of unbound material from the tumour and hence the generation of tissue contrast.

Gadolinium ($Gd^{3+}$)-chelate-based MRI contrast agents give positive contrast, which is easier to detect in the spatially and temporally heterogeneous contrast that is often found in tumours. $Gd^{3+}$-chelate-based contrast agents have been used in vitro [Jung HI et al. Bioconjug Chem. 15(5):983, 2004] and in vivo [Krishan A et al. Radiology, 246(3): 854, 2008] to successfully detect the efficacy of tumour therapy.

Contrast agents based on two biotinylated wild-type C2A domains conjugated to ($Gd^{3+}$)-labelled avidin have been tested in vitro [Neves et al., Nano Lett. 7(5): 1419, 2007].

A C2A-GST fusion protein has been labelled with $^{99m}Tc$ and used with SPECT to detect cell death in tumours following treatment [Wang, et al., Nucl. Med. Biol. 35(3): 359-364, 2008]

All of the above agents have several intrinsic limitations. The modification of wild type C2A on lysine g amino groups causes partial loss of activity. Furthermore, the modification of lysine resides generates multiple C2A species with a range of binding affinities for phosphatidylserine. Biotinylation has been shown to label wild type C2A with from 1 to 3 biotin molecules. In addition to generating multiple species, the presence of more than one biotin molecule per molecule of wild-type C2A promotes intermolecular reaction of multiple avidin molecules, generating large molecular weight conjugates which need to be removed before the contrast agent is used.

The present inventors have developed improved molecular imaging agents based on a modified synaptotagmin I C2A domain. These agents may be useful in assessing cell death in vivo, for example in tumours following cancer treatment.

An aspect of the invention provides a molecular imaging agent comprising;
  a synaptotagmin C2A domain polypeptide having a cysteine residue at a position corresponding to position 78 of SEQ ID NO:1; and,
  a detectable label attached to the cysteine residue.

The imaging agent binds to phosphatidylserine (PS) through the synaptotagmin C2A domain polypeptide. The detectable label then allows the production of images of the bound agent in vivo in an individual. Since dying cells externalise phosphatidylserine (PS) on the cell surface or expose phosphatidylserine (PS) on the inner leaflet of the plasma membrane, increased concentrations of bound imaging agent in the resulting images are indicative of tissue or areas within the individual in which cell death is occurring. In other words, the presence of apoptotic or necrotic cells at a site is indicated by increased amounts of the imaging agent at the site relative to other sites in the individual.

The synaptotagmin C2A domain polypeptide may comprise the amino acid sequence of the C2A domain of a mammalian synaptotagmin I or a variant thereof; the amino acid sequence being modified to include a cysteine residue at a position corresponding to position 78 of SEQ ID NO: 1. Preferably, the cysteine residue at the position corresponding to position 78 of SEQ ID NO: 1 is the only cysteine residue in the synaptotagmin C2A domain polypeptide.

The synaptotagmin C2A domain polypeptide having a cysteine residue at a position corresponding to position 78 of SEQ ID NO: 1 is referred to herein as "C2Am".

Attachment of the detectable label to the cysteine group of the C2A domain allows the production of the imaging agent in a homogeneous form (i.e. a single molecular species) with a single binding affinity for phosphatidylserine.

For example, the synaptotagmin C2A domain polypeptide may comprise the amino acid sequence of SEQ ID NO:1 or a variant of the amino acid sequence of SEQ ID NO:1 which retains a cysteine residue at a position corresponding to position 78 of SEQ ID NO: 1.

A variant of the C2A domain of a mammalian synaptotagmin I may have an amino acid sequence having at least 75%, at least 80%, at least 85%, at least 90%, at least 95% or at least 98% sequence identity to the sequence of the C2A domain of a reference mammalian synaptotagmin I Suitable reference mammalian synaptotagmin I sequences may include the amino acid sequence of the C2A domain of human synaptotagmin I (SYT1: GeneID 6857; nucleic acid sequence NM_005639.1 GI: 5032138; amino acid sequence NP_005630.1 GI: 5032139) or a homologue from another mammalian species, such as *Rattus norvegicus* (Syt1: GeneID: 25716 amino acid sequence P21707.3 GI: 94730428 or NP_001028852.2 GI: 148356226; nucleotide sequence NM_001033680.2 GI: 148356225). Position 78 of the C2A domain of synaptotagmin I (SEQ ID NO: 1) equates to position 217 of the full-length *Rattus norvegicus* synaptotagmin I and position 218 of the full-length human synaptotagmin I.

Suitable reference sequences include the S78C mutant C2A domain of synaptotagmin I which is shown in SEQ ID NO: 1. SEQ ID NO: 1 corresponds to the both the rat and human C2A domain amino acid sequences, which are identical.

Amino acid sequence identity is generally defined with reference to the algorithm GAP (GCG Wisconsin Package™, Accelrys, San Diego Calif.). GAP uses the Needleman &

Wunsch algorithm (J. Mol. Biol. (48): 444-453 (1970)) to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST or TBLASTN (which use the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), generally employing default parameters.

Particular amino acid sequence variants may differ from that in a given sequence by insertion, addition, substitution or deletion of 1 amino acid, 2, 3, 4, 5-10, 10-20 or 20-30 amino acids.

The position in a C2A domain which corresponds to position 78 of the C2A domain of synaptotagmin I of SEQ ID NO: 1 may be readily determined in a synaptotagmin polypeptide sequence using routine sequence analysis techniques. The amino acid at this position may be replaced by a cysteine residue using routine site-directed mutagenesis techniques (see for example, *Molecular Cloning: a Laboratory Manual:* 3rd edition, Russell et al. (2001) Cold Spring Harbor Laboratory Press).

One or more heterologous amino acids, for example a heterologous peptide or heterologous polypeptide sequence, may be joined or fused to a C2A domain sequence set out herein. For example a synaptotagmin C2A domain polypeptide may comprise a C2A domain polypeptide as described above linked or fused to one or more heterologous amino acids. The one or more heterologous amino acids may include sequences from a source other than a synaptotagmin I protein.

In some embodiments, molecular imaging agents may comprise multiple C2A domains. For example, an imaging agent may comprise one, two, three or four or more C2A domains in addition to the mutant C2A domain described above. These additional C2A domains may include one or more wild-type C2A domains which increase the avidity of the synaptotagmin C2A domain polypeptide and one or more additional S78C C2A domain mutants as described above for the incorporation of additional detectable labels into the agent.

In some embodiments, a synaptotagmin C2A domain polypeptide for use in an imaging agent may be produced by cleavage of a fusion protein comprising the synaptotagmin C2A domain polypeptide, for example using a site-specific protease such as thrombin or factor Xa. The synaptotagmin C2A domain polypeptide thus produced may comprise one or more heterologous amino acids at the N or C terminal which form all or part of the site-specific protease recognition sequence. A fusion protein may comprise a purification tag which is removed by the site-specific protease after purification. Suitable purification tags include glutathione-S-transferase (from *Schistosoma japonica*). The production of synaptotagmin C2A domain polypeptides is described in more detail below.

In some embodiments, a molecular imaging agent described herein has a molecular weight of less than less than 40 kDa, less than 30 kDa, or less than 20 kDa.

Another aspect of the invention provides an isolated binding moiety for use in an imaging agent for detecting cell death comprising;
 a synaptotagmin C2A domain polypeptide having a cysteine residue at a position corresponding to position 78 of SEQ ID NO:1;
 said cysteine residue being suitable for attaching a detectable label.

Synaptotagmin C2A domain polypeptides are described in more detail above.

Synaptotagmin C2A domain polypeptides may be generated wholly or partly by chemical synthesis. For example, polypeptides may be synthesised using liquid or solid-phase synthesis methods; in solution; or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Chemical synthesis of polypeptides is well-known in the art (J. M. Stewart and J. D. Young, Solid Phase Peptide Synthesis, 2nd edition, Pierce Chemical Company, Rockford, Ill. (1984); M. Bodanzsky and A. Bodanzsky, The Practice of Peptide Synthesis, Springer Verlag, New York (1984); J. H. Jones, The Chemical Synthesis of Peptides. Oxford University Press, Oxford 1991; in Applied Biosystems 430A Users Manual, ABI Inc., Foster City, Calif.; G. A. Grant, (Ed.) Synthetic Peptides, A User's Guide. W. H. Freeman & Co., New York 1992, E. Atherton and R. C. Sheppard, Solid Phase Peptide Synthesis, A Practical Approach. IRL Press 1989 and in G. B. Fields, (Ed.) Solid-Phase Peptide Synthesis (Methods in Enzymology Vol. 289). Academic Press, New York and London 1997).

Synaptotagmin C2A domain polypeptides may be generated wholly or partly by recombinant techniques. For example, a nucleic acid encoding a synaptotagmin C2A domain polypeptide may be expressed in a host cell and the expressed polypeptide isolated and/or purified from the cell culture.

Nucleic acid sequences and constructs as described above may be comprised within an expression vector. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Suitable regulatory sequences to drive the expression of heterologous nucleic acid coding sequences in expression systems are well-known in the art and include constitutive promoters, for example viral promoters such as CMV or SV40, and inducible promoters, such as Tet-on controlled promoters. A vector may also comprise sequences, such as origins of replication and selectable markers, which allow for its selection and replication and expression in bacterial hosts such as *E. coli* and/or in eukaryotic cells.

Vectors may be plasmids, viral e.g. 'phage, or phagemid, as appropriate. For further details see, for example, *Molecular Cloning: a Laboratory Manual:* 3rd edition, Russell et al., 2001, Cold Spring Harbor Laboratory Press. Many known techniques and protocols for expression of recombinant polypeptides in cell culture and their subsequent isolation and purification are known in the art (see for example *Protocols in Molecular Biology*, Second Edition, Ausubel et al. eds. John Wiley & Sons, 1992; *Recombinant Gene Expression Protocols* Ed RS Tuan (March 1997) Humana Press Inc).

In some embodiments, the synaptotagmin C2A domain polypeptide may be expressed as a fusion protein with a purification tag. Preferably the fusion protein comprises a protease recognition site between the synaptotagmin C2A domain polypeptide and purification tag. Following expression, the fusion protein may be isolated by affinity chromatography using an immobilised agent which binds to the purification tag. After isolation, the fusion protein may be proteolytically cleaved, for example using thrombin or factor Xa, to produce the synaptotagmin C2A domain polypeptide.

The purification tag is a heterologous amino acid sequence which forms one member of a specific binding pair. Polypeptides containing the purification tag may be detected, isolated and/or purified through the binding of the other member of the specific binding pair to the polypeptide. In some preferred embodiments, the tag sequence may form an epitope which is bound by an antibody molecule.

Various suitable purification tags are known in the art, including, for example, MRGS(H)$_6$, DYKDDDDK (FLAG™), T7-, S- (KETAAAKFERQHMDS), poly-Arg (R$_{5-6}$), poly-His (H$_{2-10}$) poly-Cys (C$_4$) poly-Phe(F$_{11}$) poly-Asp (D$_{5-16}$), Strept-tag II (WSHPQFEK), c-myc (EQKLISEEDL), Influenza-HA tag (Murray, P. J. et al (1995) *Anal Biochem* 229, 170-9), Glu-Glu-Phe tag (Stammers, D. K. et al (1991) *FEBS Lett* 283, 298-302), Tag.100 (Qiagen; 12 aa tag derived from mammalian MAP kinase 2), Cruz tag 09™ (MKAEFRRQESDR, Santa Cruz Biotechnology Inc.) and Cruz tag 22™ (MRDALDRLDRLA, Santa Cruz Biotechnology Inc.). Known tag sequences are reviewed in Terpe (2003) Appl. Microbiol. Biotechnol. 60 523-533.

In some preferred embodiments, the purification tag is glutathione-S-transferase. Following expression, a fusion protein comprising the synaptotagmin C2A domain polypeptide and glutathione-S-transferase may be isolated by affinity chromatography using immobilised glutathione. The purification of glutathione-S-transferase fusion proteins is well known in the art. After isolation, the fusion protein may then be proteolytically cleaved to produce the synaptotagmin C2A domain polypeptide.

The detectable label may be any molecule, atom, ion or group which is detectable in vivo by a molecular imaging modality. Suitable detectable labels may include metals, radioactive isotopes and radio-opaque agents (e.g. gallium, technetium, indium, strontium, iodine, barium, bromine and phosphorus-containing compounds), radiolucent agents, contrast agents and fluorescent dyes.

The choice of detectable label depends on the molecular imaging modality which is to be employed. Molecular imaging modalities which may be employed include radiography, fluoroscopy, fluorescence imaging, high resolution ultrasound imaging, bioluminescence imaging, Magnetic Resonance Imaging (MRI), and nuclear imaging, for example scintigraphic techniques such as Positron Emission Tomography (PET) and Single Photon Emission Computerised Tomography (SPECT).

In vivo fluorescence imaging techniques involve the creation of an image using emission and absorbance spectra that are appropriate for the particular fluorescent detectable label used. The image can be visualized by conventional techniques, including Fluorescence imaging techniques may include Fluorescence Reflectance Imaging (FRI), fluorescence molecular tomography (FMT), Hyperspectral 3D fluorescence imaging (Guido Zavattini et al. Phys. Med. Biol. 51:2029, 2006) and diffuse optical spectroscopy (Luker & Luker. J Nucl Med. 49(1):1, 2008).

Suitable fluorescence detectable labels include fluorescein, phycoerythrin, Europium, TruRed, Allophycocyanin (APC), PerCP, Lissamine, Rhodamine, B X-Rhodamine, TRITC, BODIPY-FL, FluorX, Red 613, R-Phycoerythrin (PE), NBD, Lucifer yellow, Cascade Blue, Methoxycoumarin, Aminocoumarin, Texas Red, Hydroxycoumarin, Alexa Fluor™ dyes (Molecular Probes) such as Alexa Fluor™ 350, Alexa Fluor™ 488, Alexa Fluor™ 546, Alexa Fluor™ 568, Alexa Fluor™ 633, Alexa Fluor™ 647, Alexa Fluor™ 660 and Alexa Fluor™ 700, sulfonate cyanine dyes (AP Biotech), such as Cy2, Cy3, Cy3.5, Cy5, Cy5.5 and Cy7, IRD41 IRD700 (Li-Cor, Inc.), NIR-1 (Dejindom, Japan), La Jolla Blue (Diatron), DyLight™ 405, 488, 549, 633, 649, 680 and 800 Reactive Dyes (Pierce/Thermo Fisher Scientific Inc) or LI-COR™ dyes, such as IRDye™ (LI-COR™ Biosciences)

Other suitable fluorescent detectable labels include lanthanide ions, such as terbium and europium. Lanthanide ions may be attached to the synaptotagmin polypeptide by means of chelates, as described elsewhere herein.

Other suitable fluorescent detectable labels include quantum dots (e.g. Qdot™, Invitrogen). Techniques for labelling proteins with quantum dots are well-known in the art (Michalet, X. et al. Science 307:538, 2005; Alivisatos, P. Nat Biotechnol 22:47-52, 2004).

Magnetic resonance image-based techniques create images based on the relative relaxation rates of water protons in unique chemical environments. Suitable MRI techniques are described in more detail in Gadian, D. 'NMR and its applications to living systems'. Oxford Univ. Press, 1995, 2$^{nd}$ edition). Magnetic resonance imaging may include conventional magnetic resonance imaging (MRI), magnetization transfer imaging (MTI), magnetic resonance spectroscopy (MRS), diffusion-weighted imaging (DWI) and functional MR imaging (fMRI) (Rovaris et al. (2001) J Neurol Sci 186 Suppl 1: S3-9; Pomper & Port (2000) Magn Reson Imaging Clin N Am 8: 691-713; Kean & Smith, (1986) Magnetic Resonance Imaging: Principles and Applications, Williams and Wilkins, Baltimore, Md.).

Labels suitable for use as magnetic resonance imaging (MRI) labels may include paramagnetic or superparamagnetic ions, iron oxide particles, and water-soluble contrast agents. Superparamagnetic and paramagnetic ions may include transition, lanthanide and actinide elements such as iron, copper, manganese, chromium, erbium, europium, dysprosium, holmium and gadolinium. Preferred paramagnetic detectable labels include gadolinium.

In some embodiments, the label may be a scintigraphic detectable label. Suitable scintigraphic detectable labels include radioisotopes, for example, positron emitting radioisotopes and gamma emitting radioisotopes Scintigraphic imaging methods include SPECT (Single Photon Emission Computed Tomography), PET (Positron Emission Tomography), gamma camera imaging, and rectilinear scanning. Scintigraphic imaging methods may comprise the use of a gamma camera or rectilinear scanner to detect radioactivity in a single plane. SPECT imaging systems may be based on the use of one or more gamma cameras that are rotated about the subject of analysis, and thus integrate radioactivity in more than one dimension. PET imaging systems may comprise an array of detectors in a ring that also detect radioactivity in multiple dimensions.

Scintigraphic detectable labels comprising positron emitting radioisotopes may be useful, for example, in Positron Emission Tomography (PET). Suitable radioisotopes include Carbon-11, Nitrogen-13, Oxygen-15, Fluorine-18, Gallium-68 and Copper-64

Scintigraphic detectable labels comprising gamma emitting radioisotopes may be useful, for example, in Single Photon Emission Computerised Tomography (SPECT). Suitable radioisotopes include Technetium-99m, Indium-111, Indium-123, Gallium-67, Thallium-201, Xenon-124.

In addition to the in vivo applications described above, imaging agents described herein may also be useful in in vitro methods, for example in flow cytometry and histochemistry assays.

A method of producing an imaging agent as described herein may comprise;

providing a synaptotagmin C2A domain polypeptide having Cys at a position corresponding to position 217 of SEQ ID NO:1; and, attaching a detectable label to the Cys residue.

The mode of attachment of the synaptotagmin C2A domain polypeptide to the detectable label will vary depending, in part, on the chemical nature of the detectable label. A range of standard conjugation techniques may be employed (see for example, Hermanson, G., 'Bioconjugate techniques', Academic Press, San Diego, USA, 1996).

The detectable label may be attached directly to the synaptotagmin C2A domain polypeptide or may be attached indirectly through one or more linker molecules.

In some preferred embodiments, the detectable label may be attached to the synaptotagmin C2A domain polypeptide via one or more covalent bonds. For example, the detectable label may be attached to the cysteine residue by means of a reactive group which reacts with the thiol group of the cysteine residue to form covalent bonds, such as thioether linkages.

Suitable thiol-reactive groups include haloacetyl and alkyl halide derivates, iodoacetamides, maleimides, aziridines, acryloyl derivatives, arylating agents, and thiol-disulfides exchange reagents. In some embodiments, a phenylmercury group may be used.

Preferably, the reactive group is a maleimido group.

The reactive group which reacts with the thiol group may be part of the detectable label (i.e. the detectable label may comprise the reactive group) or may be part of a bifunctional reagent or linker which links the detectable label and the synaptotagmin C2A domain polypeptide (i.e. the detectable label and the synaptotagmin C2A domain polypeptide may be linked via a bifunctional reagent or linker comprising the reactive group). Bifunctional reagents comprise two separate binding groups for the formation of intermolecular attachments. The bifunctional agents may be homofunctional or heterofunctional (i.e. the binding groups may be the same or different).

The bifunctional reagent may bind directly to the synaptotagmin C2A domain polypeptide and the detectable label. For example, the bifunctional reagent may comprise a thiol-reactive group which forms a covalent bond with the synaptotagmin C2A domain polypeptide and a second binding group which binds the detectable label. The second binding group may bind the detectable label via covalent or non-covalent bonds. For example, the bifunctional reagent may be a bifunctional chelate which comprises a reactive group that covalently binds to the cysteine residue of the synaptotagmin C2A domain polypeptide and a chelate group which forms a complex with the metal ion label.

Suitable reactive groups include thiol-reactive groups such as maleimido groups as described above.

Suitable chelate groups are well known in the art and may, for example, be selected from the group consisting of DTPA (diethylenetriamine-pentaacetic acid), substituted DTPA, DOTA (1,4,7,10-tetraazacyclododecane-1,4,7,10-tetraacetic acid), substituted DOTA, EDTA (ethylenediaminetetraacetic acid), substituted EDTA, CDTA (trans-1,2-cyclohexylene-dinitrilotetraacetic acid) substituted CDTA, $H_4$-TETA (1,4,8,11-tetraazacyclotetradecane-1,4,8,11-tetraacetic acid) and NOTA (1,4,7-triazacyclononane-1,4,7-triacetic acid).

In some embodiments, the detectable label may be chelating to the synaptotagmin C2A domain polypeptide using a chelating peptide. Suitable chelating peptide sequences are well known in the art (see for example WO2006107794; U.S. Pat. No. 5,594,115; WO/1993/023425; Smith et al J. Biol. Chem. (1988) 263 15 7211; Tian et al J. Nucl. Med. 45 12 2070-2082; Kievens et al Biophysical Journal 64: 919-924 (1993))

Preferred bifunctional chelates include maleimido-monoamide-DOTA.

The bifunctional chelate may be reacted with the detectable label and the synaptotagmin C2A domain polypeptide by any convenient technique. For example, the chelate group of the bifunctional chelate may be chelated with the metal ion label to form a metal-chelate complex before, after or simultaneously with the reactive group of the bifunctional chelate being reacted with the synaptotagmin C2A domain polypeptide.

The procedure for attaching the metal ion label to the chelate will depend on the bifunctional chelate and the metal ion used, as well as the specific activity and quantity required for the application. Suitable methods are known in the art and are described, for example in Sosabowski, J. & Mather, S. (2006) Nat Protoc 1(2):972-6 and Cooper M. et al (2006) Nat Protoc 1(1):314-7. For example, for the chelation of trivalent metal ions, such as $^{111}$In, by DOTA, the synaptotagmin C2A domain polypeptide may be transferred to a slightly acidic buffer. The trivalent metallic isotope may then be added, incubated for 1 hour at 37° C. to allow the labelling reaction to occur and then quenched using EDTA. Labelling efficiency may be monitored by thin layer chromatography. Preferably, labelling efficiency is >95%. Further purification of the labelled species from unbound metal may be achieved, for example, by size-exclusion high performance liquid chromatography (HPLC).

Some preferred imaging agents may comprise;

a synaptotagmin C2A domain polypeptide having a cysteine residue at a position corresponding to position 78 of SEQ ID NO:1; and, a detectable label attached to the cysteine residue, wherein the detectable label is a gadolinium ion.

The gadolinium ion may be bound to a chelate, such as DTPA (Diethylene triamine pentaacetic acid) or DOTA (1,4,7,10-tetraazacyclododecane-1,4,7,10-tetraacetic acid), in a metal-chelate complex.

The gadolinium-chelate complex may be attached to the cysteine residue by a thioether bond. For example, the chelate may further comprise a maleimide group (i.e. in a bifunctional reagent) which reacts with the cysteine residue to form a thioether bond.

In some embodiments, the bifunctional reagent may bind to synaptotagmin C2A domain polypeptide and a second linker, which binds the detectable label. For example, the second linker may comprise a chemical group which may be labelled with a PET isotope e.g. Fluorine-18.

In some embodiments, click-chemistry may be employed. Click-chemistry involves the CuI-catalysed coupling between two components, one containing an azido group and the other a terminal acetylene group, to form a triazole ring. Since azido and alkyne groups are inert to the conditions of other coupling procedures and other functional groups found in peptides are inert to click chemistry conditions, click-chemistry allows the controlled attachment of almost any linker to the synaptotagmin C2A domain polypeptide under mild conditions.

For example, the cysteine residue of the synaptotagmin C2A domain polypeptide may be reacted with a bifunctional reagent containing a thiol-specific reactive group at one end (e.g. iodoacetamide, maleimide or phenylthiosulfonate) and an azide or acetylene at the other end. Label groups may be attached to the terminal azide or acetylene using click-chemistry. For example, a second linker with either an acetylene or azide group on one end of a linker and a chelate (for metal isotopes) or leaving group (for halogen labelling) on the other end (Baskin, J. (2007) *PNAS* 104(43)16793-97) may be employed.

Another aspect of the invention provides a method of imaging cell death in an individual comprising;
  administering an imaging agent as described above to an individual, and;
  producing one or more images of the distribution of the imaging agent within the individual.

Images may, for example, be produced over a period of time (i.e. at intervals) after administration of the agent.

The amount of imaging agent at a site in the individual is indicative of the amount of cell death at the site. For example, an increased amount of imaging agent at a target site relative to other sites is indicative of increased cell death at the target site.

Related aspects provide an imaging agent for use in a method of imaging cell death in vivo and the use of an imaging agent for the manufacture of a preparation for use in a method of imaging cell death in vivo.

The administration of an imaging agent to an individual is described in more detail below.

One or more images of the distribution of the imaging agent within the individual may be produced using a molecular imaging technique. Any molecular imaging technique which detects the detectable label of the imaging agent may be employed. For example, MRI may be employed to detect an imaging agent containing an MRI detectable label. A range of suitable molecular imaging techniques are known in the art.

Phosphatidylserine (PS) is externalised at the surface of cells undergoing cell death. Following administration, the synaptotagmin C2A domain polypeptide of the imaging agent binds to phosphatidylserine (PS) which is exposed on cells, for example PS which is externalised or exposed on the inner leaflet of the plasma membrane surface, thereby labelling cells which are undergoing or have undergone cell death.

Using an appropriate molecular imaging technique, one or more images may be produced which show the distribution of the detectable label within all or part of the individual over a period of time after administration of the agent. The amount or concentration of detectable label in a tissue or region of the body is indicative of the amount of cell death in the tissue or region. Increased concentrations of detectable label in a tissue or region of the body are indicative that the cells in the tissue or region are undergoing increased cell death, relative to other tissues or regions in the body. For example, an increased concentration of detectable label at a tumour or other cancerous tissue in the body is indicative that the cells in the tumour or other cancerous tissue are undergoing increased cell death, relative to other tissues or regions in the body. Imaging agents of the invention may therefore be useful in imaging cell death in tumours following treatment.

Another aspect of the invention provides a method of imaging a tumour in an individual comprising;
  administering an imaging agent as described above to an individual having a tumour, and;
  producing one or more images of the distribution of the imaging agent at the site of the tumour in the individual.

In some embodiments, the speed of onset and extent of cell death, for example in a tumour following cancer therapy, may be determined using imaging. This may be useful, for example, in predicting the outcome of cancer therapy. (Brindle, K. (2008) *Nat Rev Cancer* 8(2):94-107; Neves, A. A. & Brindle, K. M. (2006) *Biochim Biophys Acta* 1766(2): 242-61).

A method of determining the effectiveness of a cancer therapy in treating a tumour in an individual may comprise;
  administering an imaging agent as described above to an individual during or after cancer therapy; and,
  producing one or more images of the distribution of the imaging agent at the site of the tumour in the individual.

One or more images of the distribution of the imaging agent at the site of the tumour in the individual during or after cancer therapy may be produced.

The imaging agent may be administered to the individual before cancer therapy and one or more images of the distribution of the imaging agent at the site of the tumour in the individual before cancer therapy produced.

The images of the distribution of the imaging agent at the site of the tumour may be used to determine the amount or extent of binding of the imaging agent to the tumour. Conventional chemo- and radiotherapies, when successful, normally induce extensive local cell death in tumours. This cell death can be imaged by the imaging agent. Increased binding of the imaging agent to the tumour following the cancer therapy may be indicative that the cancer therapy is effective in treating the tumour.

Increased binding may be determined relative to binding to the tumour before the cancer therapy or relative to binding to non-tumour tissue.

For example, the distribution of the imaging agent at the site of the tumour during or after treatment may be compared with the distribution before treatment. An increased density or distribution of the imaging agent during or after treatment, relative to before treatment is indicative that the cancer therapy is effective in treating the tumour.

Suitable cancer therapies are well-known in the art and include radiotherapy and chemotherapy.

An increased concentration of detectable label in a tissue or site in the body is indicative that the cells in tissue or site are undergoing increased cell death relative to other tissues or site in the body, for example as a result of a disease condition characterised by increased cell death, such as inflammation, infection, cardiac infarction or cardiac plaque formation. Imaging agents of the invention may therefore be useful in imaging cell death following treatment for such conditions.

Another aspect of the invention provides a method of assessing a disease condition characterised by increased cell death in an individual comprising;
  administering an imaging agent as described above to the individual, and;
  producing one or more images of the distribution of the imaging agent in the individual.

In some embodiments, the speed of onset and extent of cell death may be determined using imaging. This may be useful, for example, in assessing the condition, for example to determine the extent or severity of the condition, its prognosis and/or its responsiveness to therapy.

A method of determining the effectiveness of a therapy in treating disease condition characterised by increased cell death in an individual may comprise;
  administering an imaging agent as described above to an individual during or after therapy; and,
  producing one or more images of the distribution of the imaging agent in the individual.

The images of the distribution of the imaging agent may be used to determine the amount or extent of binding of the imaging agent to dead or dying cells in the individual. Decreased binding or a reduction in the number of sites at which increased binding occurs following the therapy may be indicative that the therapy is effective in reducing the amount of cell death and thereby treating the disease condition.

Increased or decreased binding may be determined relative to controls. Suitable control experiments would be apparent to the skilled person and may, for example, include binding before the therapy or relative to binding to healthy tissue, as appropriate.

An imaging agent described herein may be used to assess drug efficacy in early stage clinical trials and subsequently in the clinic, where it could be used to guide treatment. Ineffective treatments could be abandoned at an early stage, allowing the selection of more effective drugs (see for example, Brindle, K. (2008) Nat Rev Cancer 8(2):94-107).

A method for determining the efficacy of a treatment regimen for an individual may comprise:

(a) subjecting the individual to an initial regimen of treatment, and;
(b) determining the amount or extent of binding of an imaging agent described herein to dead or dying cells in the individual,
wherein a change in the amount or extent of binding in response to the regimen is indicative that the regimen is efficacious in the individual.

If the initial regimen of the treatment is insufficient to cause a change in the amount or extent of binding of the imaging agent, the regimen may be altered or adjusted until the amount or extent of binding of the imaging agent in the individual changes. A method may thus comprise the further steps;

(c) altering the regimen of treatment and subjecting the individual to the altered regimen;
(d) determining the amount or extent of binding of an imaging agent described herein to dead or dying cells in the individual, and
(e) repeating steps c) and d) until a change in the amount or extent of binding of the imaging agent is observed,
wherein a change in the amount or extent of binding of the imaging agent in response to the regimen is indicative that the regimen is efficacious in the individual.

In some embodiments, step (e) may comprise repeating steps c) and d) until the amount or extent of binding of an imaging agent changes beyond a predetermined value,
wherein a change in the amount or extent of binding of the imaging agent beyond the predetermined value is indicative that the regimen is efficacious in the individual.

The individual may have a cancer condition and the treatment may be a cancer treatment such as radiotherapy or chemotherapy. An increase in the amount or extent of binding of the imaging agent to tumour tissue in response to the regimen is indicative that the regimen causes cell death in the tumour tissue and is therefore efficacious in the individual.

The individual may have a disease condition characterised by cell death. A decrease in the amount or extent of binding of the imaging agent to one or more disease sites in the individual in response to the regimen is indicative that the regimen ameliorates cell death at the sites and is therefore efficacious in the individual.

Related aspects provide an imaging agent as described herein for use in any of the above methods and the use of an imaging agent as described herein for the manufacture of a preparation for use in any of the above methods.

While it is possible for an imaging agent to be administered alone, it is preferable to present it as a pharmaceutical composition (e.g., formulation) comprising the imaging agent as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Pharmaceutical compositions comprising an imaging agent admixed or formulated together with one or more pharmaceutically acceptable carriers, excipients, buffers, adjuvants, stabilisers, or other materials, as described herein, may be used in the methods described herein.

Another aspect of the invention provides a method of preparing a pharmaceutical composition comprising
providing an imaging agent as described above and
admixing the imaging agent with a pharmaceutically acceptable excipient.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods well-known in the art of pharmacy. Such methods include the step of bringing the imaging agent into association with a carrier which may constitute one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

The imaging agent or pharmaceutical composition comprising the imaging agent) may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

In preferred embodiments, the imaging agent or pharmaceutical composition comprising the imaging agent) is administered to a subject by intravenous or intraocular injection.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example, from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use.

It will be appreciated that appropriate dosages of the imaging agent, and compositions comprising the imaging agent, can vary from patient to patient. Determining the optimal dosage will generally involve the balancing of the level of diagnostic benefit against any risk or deleterious side effects of the administration. The selected dosage level will depend on a variety of factors including, but not limited to, the route of administration, the time of administration, the rate of excretion of the imaging agent, the amount of contrast required, other drugs, compounds, and/or materials used in combination, and the age, sex, weight, condition, general health, and prior medical history of the patient. The amount of imaging agent and route of administration will ultimately be at the discretion of the physician, although generally the dosage will be to achieve concentrations of the imaging agent at a site, such as a tumour, a tissue of interest or the whole body, which allow for imaging without causing substantial harmful or deleterious side-effects.

Administration in vivo can be effected in one dose, continuously or intermittently (e.g., in divided doses at appropriate intervals). Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the physician.

As described above, the imaging agent, and compositions comprising the imaging agent may be administered before and in combination with or after cancer therapy, in order to assess the efficacy of the therapy. Suitable dosage regimens for assessing the efficacy of a therapy, for example a cancer therapy, in an individual may be selected by the treating physician.

Another aspect of the invention provides a kit for imaging of cell death as described herein. A kit may comprise a two-vial system of a lyophilized imaging agent as described herein and an aqueous diluent, comprising (a) a first vial comprising lyophilized imaging agent; and (b) a second vial comprising a pharmaceutically acceptable diluent.

The kit may include instructions for use of the imaging agent, e.g. in a method of imaging cell death in vivo.

Various further aspects and embodiments of the present invention will be apparent to those skilled in the art in view of the present disclosure. All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures and tables described below.

The corresponding dissociation constants (KD) obtained were 48.5±3.5 nM (C2A wild-type) and 49.4±4.9 nM (C2Am). Data for each concentration in duplicates.

Figure 12:
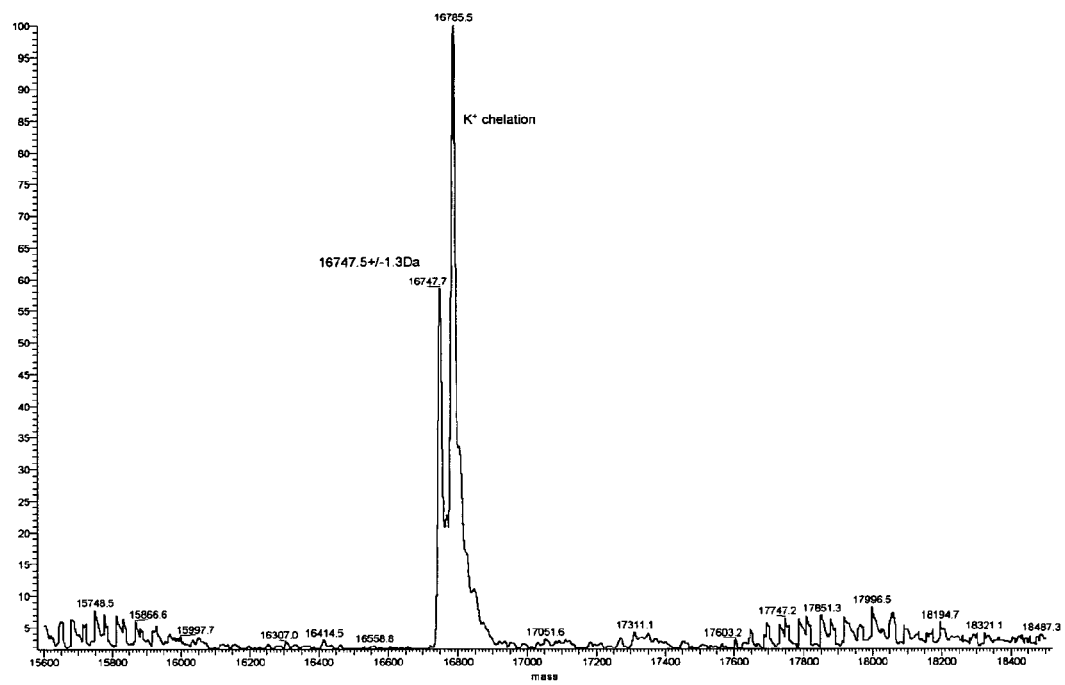

FIGS. 9 to 12 show mass spectrometry analysis (ESI) of C2A wild type (FIG. 9), C2Am (FIG. 10), C2Am-AlexaFluor488 (FIG. 11) and C2Am-DOTA (FIG. 12).

Figure 13:
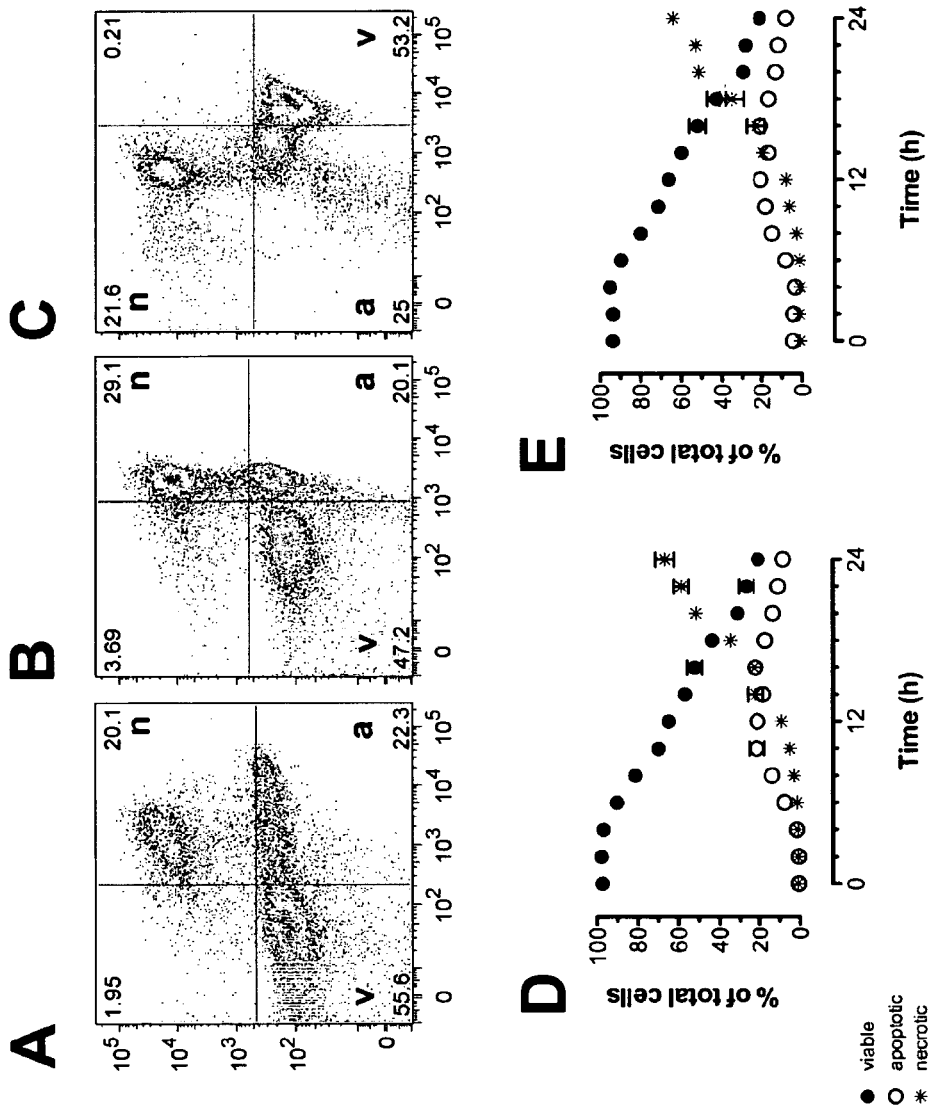

FIG. 13 shows C2Am-AF647 or AnxV-AF647 labeling of dying cells. Dual scatter Plots of cellular viability (Sytox® Green nuclear stain, a cell death marker; Exc, λ=504; Em, λ=523 nm, y-axis;) as a function of C2Am (A) or AnxV (B) labeling (Alexa Fluor® 647 channel; Exc, λ=647; Em, λ=670 nm, x-axis). Representative plots obtained for EL4 cells treated for 16 hours with etoposide (5 μM). The quadrants (red crosses) in (A) and (B) represent necrotic (n), apoptotic (a) and viable (v) cells. A dual scatter plot of Sytox® Green (y-axis) as a function of NADH autofluorescence (Exc, λ=350; Em, λ=475 nm, x-axis) is also shown (C) for the same time point after drug treatment (16 h). A time course of EL4 cell death detection using C2Am (D) or AnxV (E) is shown. Samples were collected every two hours and analyzed by flow cytometry. Four-quadrant gating, based on the population separation displayed by each protein, was used to calculate the percentage fraction of viable, apoptotic and necrotic cells. The experiment was performed three times and the data shown corresponds to a representative data set (each time point in triplicate). Data shown are means±SEM (n=3 replicates, error bars lie within the symbols when not visible) for each time point. [C2Am]=0.2 μM, [AnxV]=4 nM. The figures in the external corner of each quadrant represent the respective percentage cell fraction.

Figure 14:
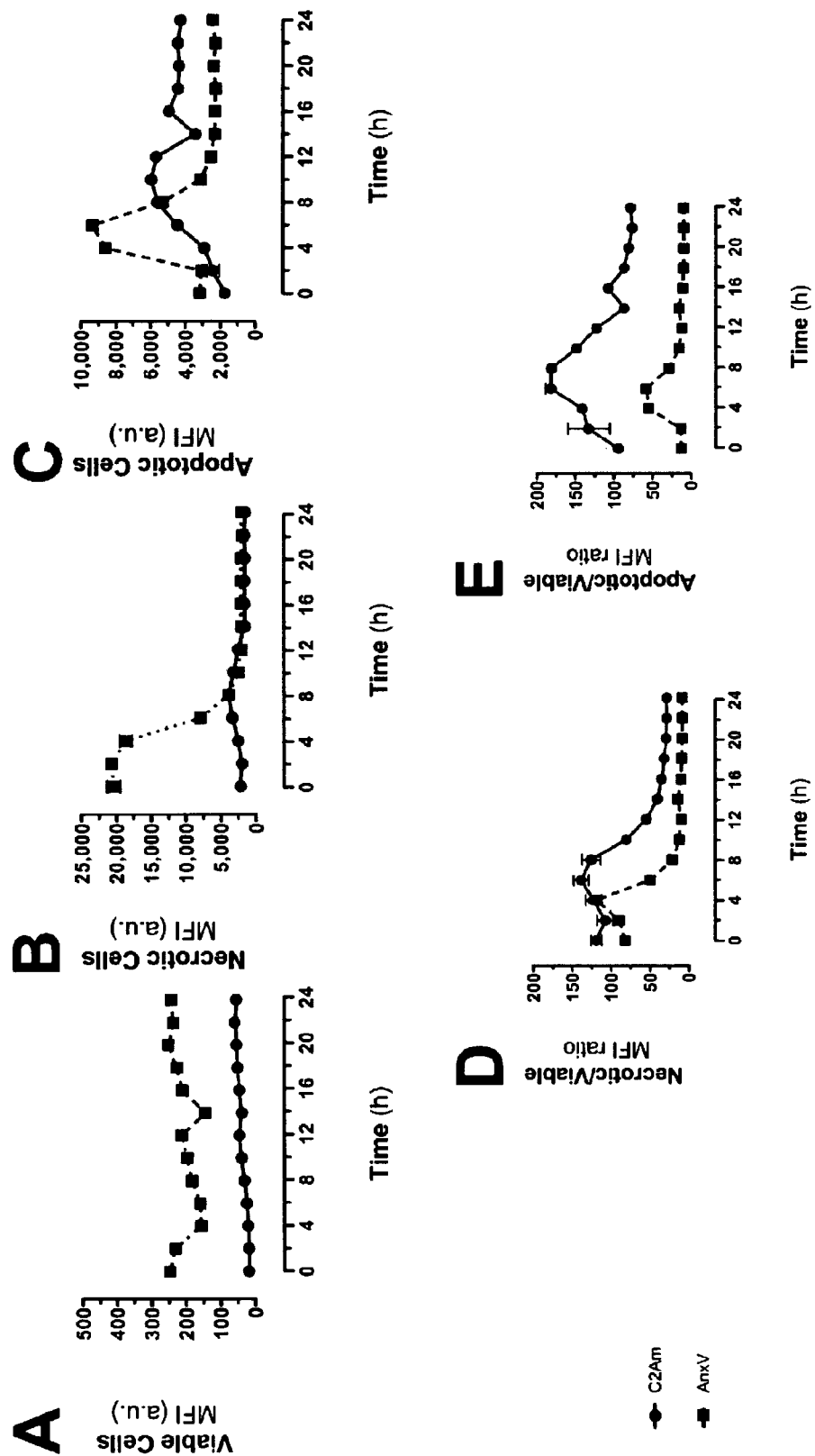

FIG. 14 shows a time course of fluorescent labeling of EL4 cells using C2Am (A) or AnxV (B). Mean fluorescent intensity (MFI) for viable (A), necrotic (B) and apoptotic (C) cells, labeled with C2Am (closed circles) and AnxV (closed squares). Data gated as in FIG. 13. The experiment was performed three times and the data shown corresponds to a representative data set (each time point in triplicate). Data shown are means±SEM (n=3 replicates, error bars lie within the symbols when not visible) for each time point. [C2Am]=0.2 μM, [AnxV]=4 nM.+P<0.0001 for viable cells, at all times, for necrotic cells at t≤6 h, for apoptotic cells at t=4, 6, 10, 12, 16-24 h, * P<0.001, for apoptotic cells at t=14 h. Mean fluorescence intensity (MFI) in arbitrary units, standardized to autofluorescence levels for the respective channel. A time course of selective labeling of dying EL4 cells versus viable cells, using C2Am (D) or AnxV (E) is shown. Data are shown as the ratios of MFI, for necrotic/viable (D) and apoptotic/viable (E). The experiment was performed three times and the data shown corresponds to a representative data set (each time point in triplicate). Data shown as means±SEM (n=3 replicates, error bars lie within the symbols when not visible) for each time point. [C2Am]=0.2 μM, [AnxV]=4 nM.+ P<0.0001, for necrotic/viable ratio at t≥10 h and for apoptotic/viable ratio at t=0, 4-20 h, ** P<0.001, for apoptotic/viable ratio at 22 h and necrotic/viable ratio at 6-8 h, * P<0.05, for necrotic/viable ratio at 0 h and apoptotic/viable ratio at 2 h.

Figure 15:
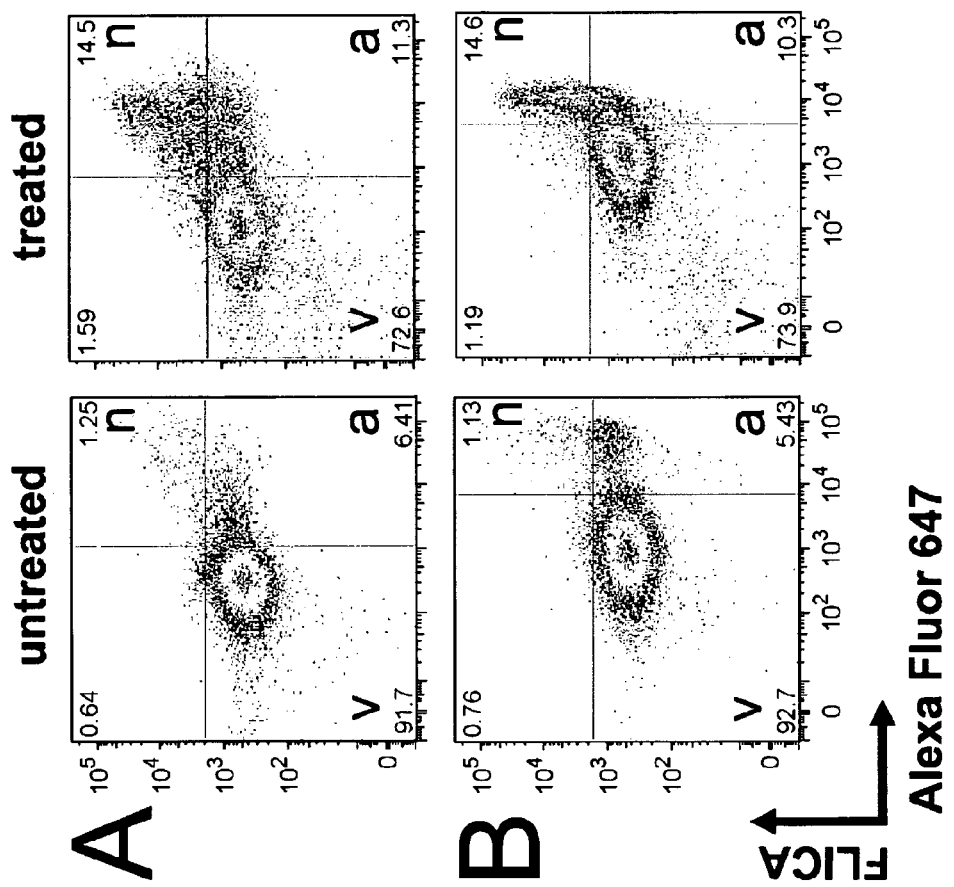

FIG. 15 shows Dual scatter plots of active caspase labelling (Poly Caspases FLICA® carboxyfluorescein; Exc, λ=490; Em, λ=530 nm, y-axis;) as a function of C2Am (A) or AnxV (B) labeling (Alexa Fluor® 647; Exc, λ=647; Em, λ=670 nm, x-axis) in untreated and 16 hour etoposide-treated EL4 cells. Apoptotic and necrotic cells, in either the untreated or treated cohorts, stained up to 2-fold and 16-fold more, respectively, with FLICA, compared with viable cells. The quadrants (red crosses) in (A) and (B) represent necrotic (n), apoptotic (a) and viable (v) cells. The figures in the external corner of each quadrant represent the respective percentage cell fraction.

Figure 16:
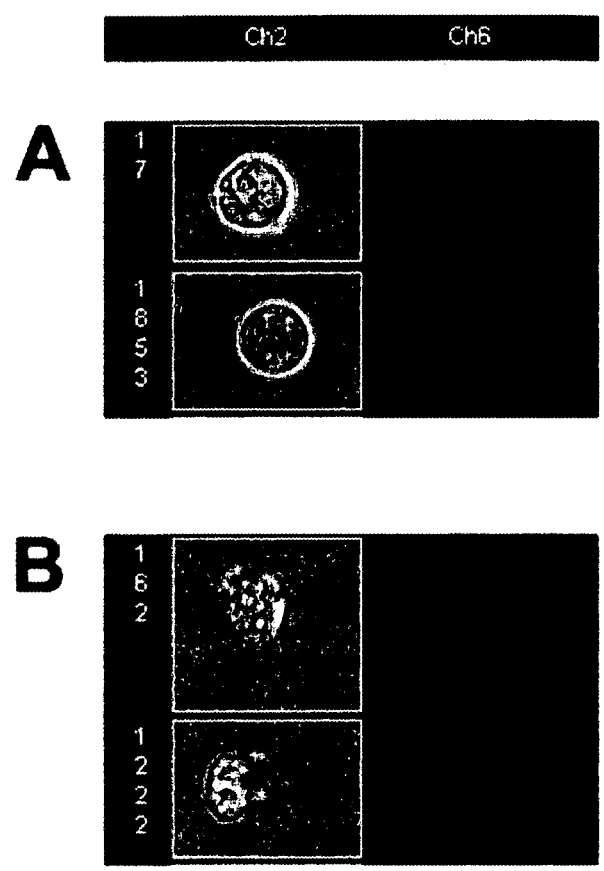

FIG. 16 shows EL4 cells, which show C2m-AF647 binding to dying (B) but not to viable (A) cells. Bright field images (left panels, under channel Ch2) and fluorescence images of the corresponding EL4 cells (right panels, under channel Ch6) were acquired. Images of cells that failed to stain with C2Am (A) appeared to be viable with a rounded regular morphology in the corresponding bright field image. Cells that stained positive with C2Am (B), had an irregular morphology and appear to be undergoing cell death in the corresponding bright field image.

Figure 17:
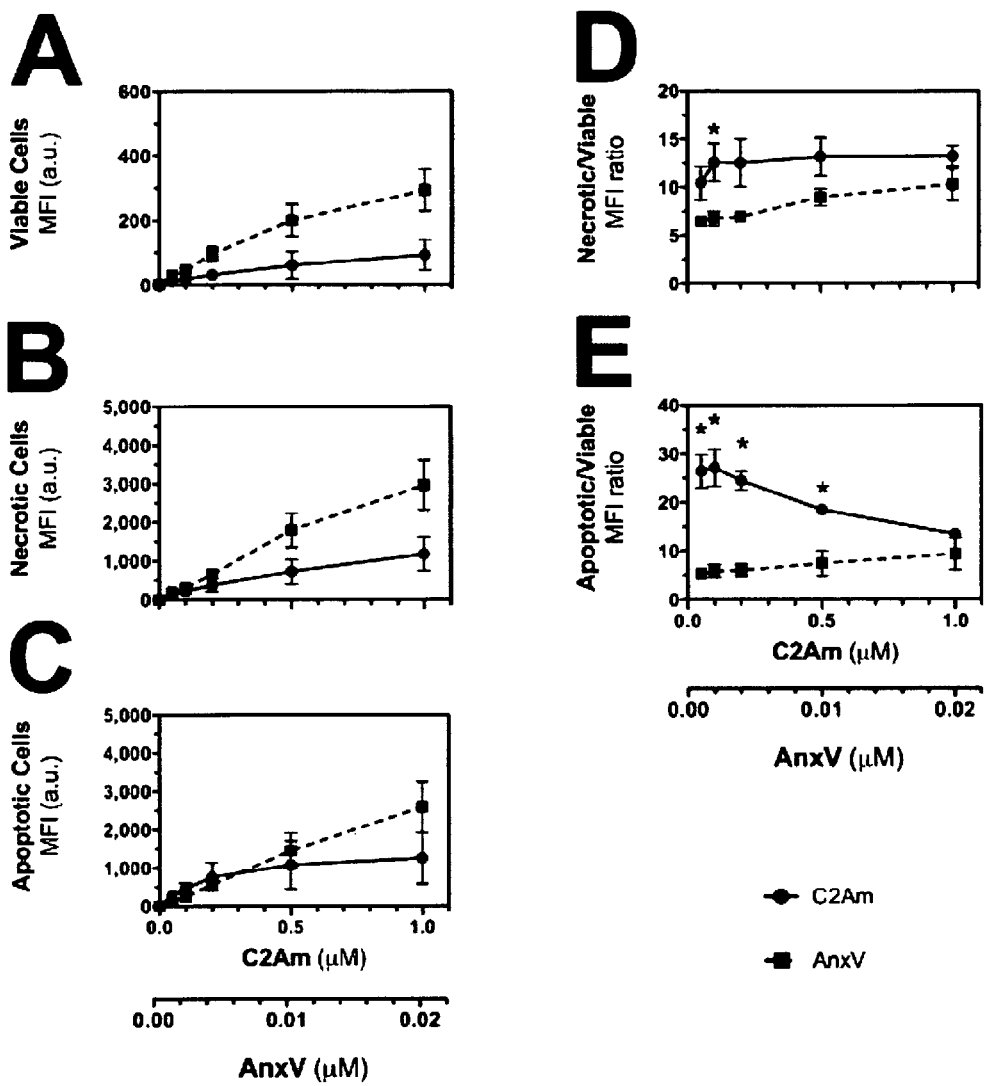

FIG. 17 shows the effect of probe concentration on labeling of EL4 cells using C2Am (closed circles) or AnxV (closed squares). The concentration ranges studied were 0.05-1.0 μM and 1-20 nM respectively, for C2Am and AnxV. Mean fluorescent intensity (MFI) data for viable (a), necrotic (b) and apoptotic (c) EL4 cells labeled by C2Am and AnxV are shown. Mean fluorescence intensity (MFI) data in arbitrary units, standardized to autofluorescence levels for the respective channel. Data are also represented as ratios of MFI, necrotic/viable (d) and apoptotic/viable (e). Data were gated using the NAD(H) autofluorescence levels, as in FIG. 13C. The experiment was performed three times and the data shown correspond to the mean results from all experiments (each concentration in the series was performed in duplicate). Data shown as means±SEM (n=3 replicates, error bars lie within the symbols when not visible) for each concentration. * P<0.05.

Figure 18:
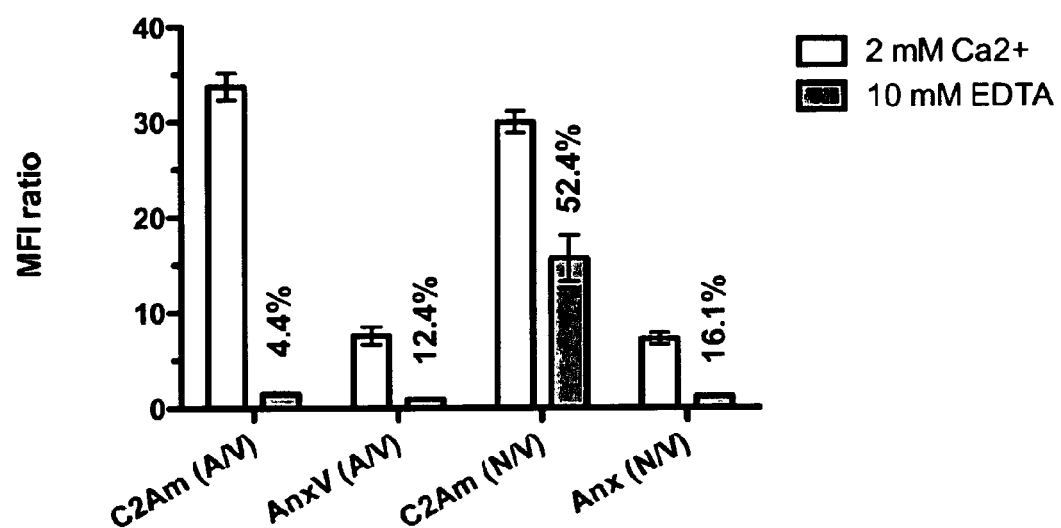

FIG. 18 shows an investigation of the calcium-dependency of binding of the two probes to apoptotic and necrotic EL4 cells. The MFI ratios of apoptotic/viable and necrotic/viable in the presence (white bars) or absence of calcium (10 mM EDTA; grey bars) are shown. The ratios obtained in the absence of calcium are also shown as a % of the ratios obtained in the presence of calcium (vertical labels over the bars).

Figure 19:
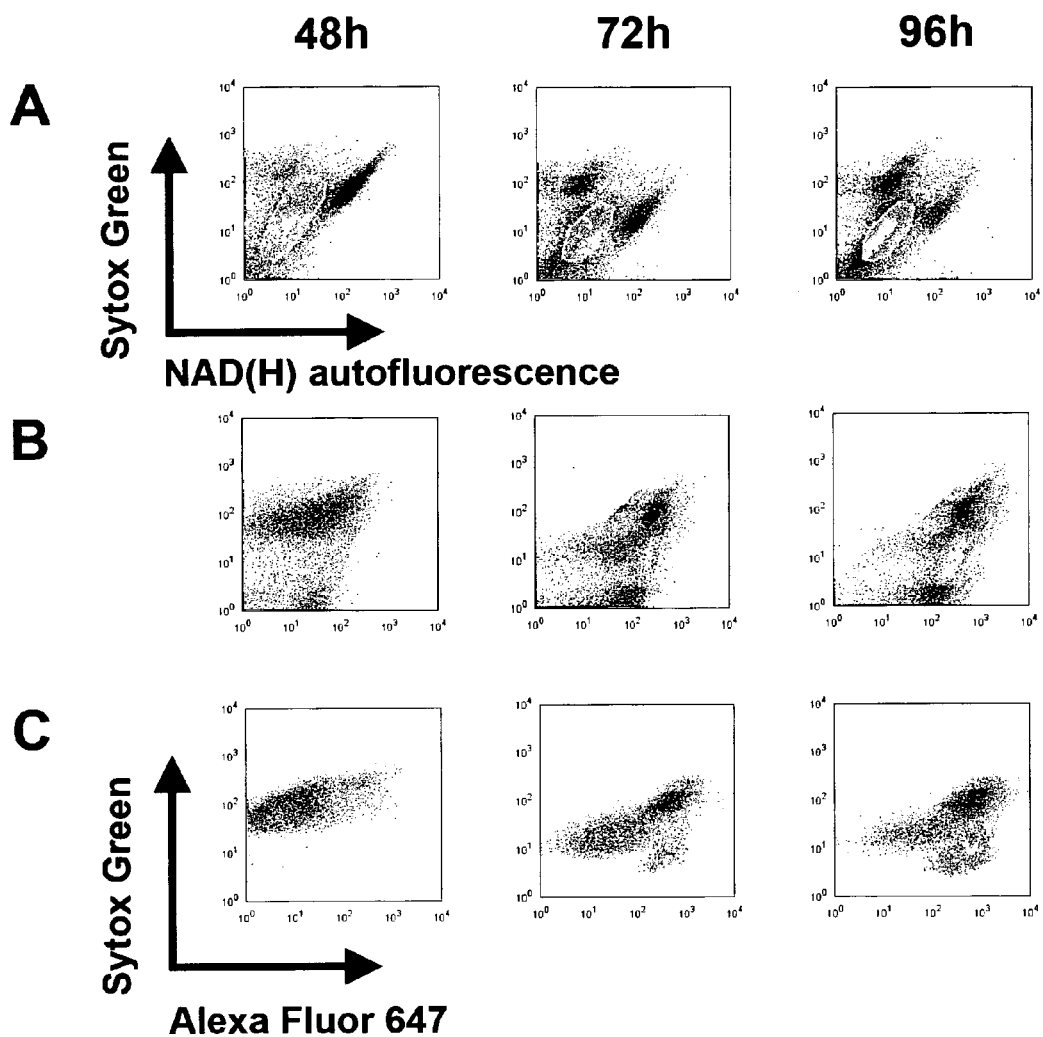
Figure 19:
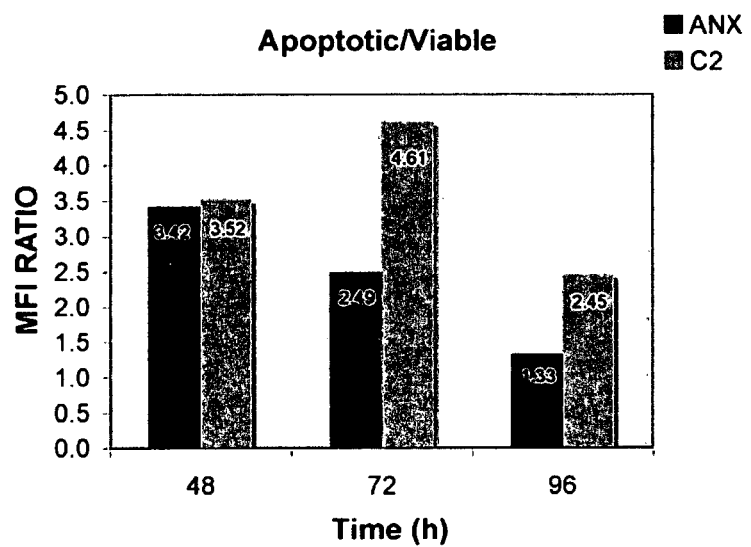
Figure 19:
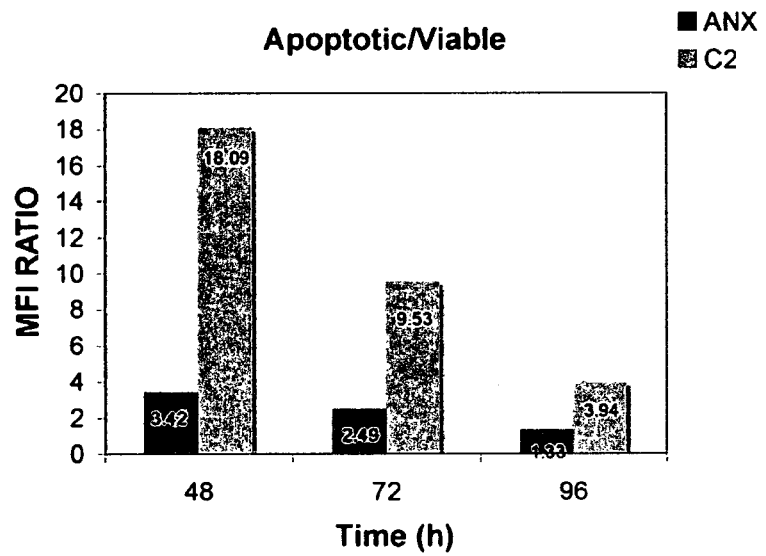

FIG. 19 shows a time course of fluorescent labeling of MDA-MB-231 cells using C2Am (C) or AnxV (B). Data gated as in FIG. 13, based on the NAD(H) autofluorescence profiles (A) of viable (blue), apoptotic (yellow) and necrotic (red) cells. The data shown are a representative data set. [C2Am]=0.2 μM, [AnxV]=4 nM. The ratios of MFI are shown for apoptotic/viable (D) and necrotic/viable (E).

Table 1 shows a comparison of the extent of EL4 cell death identified by C2Am or AnxV versus that determined by measurements of NAD(H) UV autofluorescence from the data shown in FIG. 14. x and y represent the slope and intercept, respectively, of the best fit lines of the cell fraction, detected by each protein, with that determined from measurements of NAD(H) autofluorescence; a value of slope (x) below 1 indicates an underestimate of the given cell fraction. $R^2$-correlation factor for best fit in the range analyzed (% cells).

Table 2 shows dissociation constants (Kd) derived from affinity and kinetic analysis of the SPR data for the unmodified protein C2Am and for the protein following modification (C2Am-AlxAF647). The affinity analysis for C2Am (duplicate injections) indicated a Kd of approximately 55±3.5 nM. The kinetic analysis yielded a very similar value. The modified protein C2Am-AlxAF647 displayed a slightly higher Kd of 71±6.9 nM according to the affinity analysis and 87.9 nM according to the kinetic analysis. The kinetic and affinity analyses yielded similar values. The analysis suggested that the activity of the protein was largely preserved after chemical modification.

SEQ ID NO: 1 shows the amino acid sequence of the Ser78Cys mutant C2A domain.

SEQ ID NO: 2 shows the nucleotide sequence encoding the Ser78Cys mutant C2A domain (C2Am).

SEQ ID NO: 3 shows the nucleotide sequence of a pGEX-2T vector with inserted GST/C2A domain fusion. pGEX-2T sequence, nucleotides 1-257 and 1374-6379; GST domain: nucleotides 258-917; linker: nucleotides 918-970; C2 domain: nucleotides 971-1364 (mutations: 1213-1214); artefact: nucleotides 1365-1373; GST lac promotor: −10: nucleotides 205-211; −35: nucleotides 183-188; lac operator=nucleotides 217-237; ribosome binding site=244 start codon=258.

EXPERIMENTS

Materials and Methods

All tissue culture reagents, SYTOX® Green dead cell stain, Annexin V-Alexa Fluor647™ (AnxV-AlxF647) were from Invitrogen (Paisley, Renfrewshire, UK). The green Polycaspases FLICA® kit was from Immunochemistry technologies LLC (Bloomington, Minn., USA). Analysis of the AnxV-AlxF647 preparation by SDS-PAGE showed a band with a mass slightly less than 37 kDa, which was the only band that fluoresced when illuminated with light at 633 nm. Densitometry of the Coomassie-stained gel showed that this band represented ~2% of the total protein mass in the gel, which a Non-Interfering Protein Assay® (Merck Chemicals Ltd, Nottingham, UK) indicated contained 16 μg/ml or ~460 nM AnxV-AlxF647. All chemicals were of analytical grade from Sigma-Aldrich Co. Ltd (Poole, Dorset, UK) unless stated otherwise. Etoposide (EPOSIN) from was from PCH Pharmachemie, (Haarlem, Netherlands). Murine lymphoma (EL-4) cells and human breast carcinoma cells (MDA-MB-175 cells) were obtained from the American Type Culture Collection (Teddington, UK).

Site-Directed Mutation

The *Rattus norvegicus* synaptotagmin sequence was acquired using the NCBI Genbank service (sequence identity NM_001033680; NM_001033680.2) and the C2A domain was selected from this sequence. Three candidate cysteine mutants were selected at: Ser217, Gln154, Asn248 (see FIG. 2). Appropriate primers for mutagenesis were designed with the use of Quikchange Primer Design software. The C2A-containing pGEX-2T vector (GE Healthcare, Chalfont St Giles, UK) was isolated from BL21 *E. coli* cells and underwent a double restriction digest to confirm its identity. Mutagenesis was performed by the Stratagene QuikChange Site-Directed Mutagenesis kit. *E. coli* DH5α competent cells were transformed with the mutant plasmid by heat shock and the amplified vector then isolated and sequenced. Finally, *E. coli* BL21 cells were transformed with the vector by electroporation.

Test of Protein Over-expression

In order to assess the protein over-expression yield of the three mutants, *E. coli* BL21 containing the mutated C2A vectors (2 clones for each mutant), were grown in LB medium (Merck Biosciences) in 2-liter conical flasks. The expression of the mutants was compared with wild-type GST-C2A-expressing bacteria as a control. The cell cultures were induced with IPTG (Isopropyl β-D-1-thiogalactopyranoside, GE Healthcare) when the optical density (OD at 600 nm) was 0.6, 0.8 and 1.0. Samples were collected before induction and every hour after induction and this was followed by cell lysis. SDS-PAGE gels showed bands at the expected molecular weight of 42 kDa (for GST-C2Am) for all three mutants (FIG. 3), and indicated that there were no significant differences in yield between the three induction times.

In order to compare the relative expression yields of the different mutants the experiment was repeated with one clone per mutant, induced at OD 0.7-0.8, grown for 3 hours. Cell pellets were lysed and final volumes equalised. The results of SDS-PAGE of these cell lysates are shown in FIG. 3.

Selection of Mutant Ser217Cys

S217C (position 78 of the C2A domain; position 217 of full-length Synaptotagmin I) mutant was selected as the best expressed site-directed mutant of C2A (C2Am).

The C2Am protein was expressed as a fusion protein with glutathione-S-transferase (GST). Purification of GST-C2A is described in reference 2. Briefly, GST-C2Am was extracted from lysed cells by GST-affinity chromatography (GSTprep column, GE Healthcare) and then incubated with thrombin and purified on a HiTrap sepharose column (GE Healthcare). FIG. 5 shows an SDS PAGE gel of these purification steps. Lane A shows the non-bound fraction ("flow-through") of the lysed cells on a GST column. Lane B shows the 16-kDa band representing the C2A domain and the 26 kDa band of the GST domain. This is the result of thrombin cleavage of GST-C2Am. Lane C shows the flow-through of the HiTrap sepharose column, and lane D represents the eluted C2Am domain. Finally, lanes D and E show that the molecular weight of the C2Am and wt C2A are the same.

Purification of Mutant C2A

C2Am protein was expressed as a 42-kDa GST-tagged fusion protein, following IPTG induction, and the S78C mutant was purified using affinity chromatography. Cells were cultured at 37° C. in LB medium (Gibco, Invitrogen, Grand_Island, N.Y.) containing 50 μg mL-1 ampicillin. GST-C2Am expression was induced at an optical density of ca. 1-1.2 O.D. units (at 600 nm), with 0.1 mM of isopropyl-β-D-thiogalactoside (IPTG, Amersham, Piscataway, N.J.). Induction was allowed to_proceed for 5 hours before the cells were harvested by centrifugation (15000 g, 30 minutes, 4° C.) and kept as a frozen pellet at −20° C., for 24 hour. The cell pellet was resuspended in phosphate buffered-saline (PBS, Oxoid USA, Columbia, Md.) containing 2 mM 4-(2-Aminoethyl) benzenesulphonyl fluoride (AEBSF, Melford Laboratories, Chelsworth, Ipswich, UK) and a protease inhibitor cocktail (Roche Diagnostics Ltd., Lewes, East Sussex, UK). The cells were disrupted using 3 flowcycles at 1,000 bar through a water-cooled EmulsiFlex-C5 homogenizer (Avestin, Ottawa, Ontario, Canada) and then DNAse I (ca. 250 μg) (Sigma, St. Louis, Mo.) and octyl phenol ethoxylate (Triton X-100™, final concentration of 0.1%) were added with gentle stirring (15 minutes, 4° C.). Cell debris was removed by centrifugation (40000 g, 30 minutes, 4° C.) and the remaining supernatant filtered through 0.22-μm low protein-binding filters (Millipore, Bedford, Mass., USA), before chromatographic purification. An initial purification was performed by FPLC on a GSTPrep™ FF column (GE Healthcare, Piscataway, N.J., USA), using PBS and 25 mM glutathione (Melford) in 50 mM tris(hydroxymethyl)aminomethane buffer (Trizma™ base, Sigma), pH 8.0, as loading and elution buffers, respectively. A second protein purification was performed on a HiPrep™ SP FF column (GE Healthcare) using HEPES (N-2 Hydroxyethylpiperazine-N'-2-ethanesulfonic acid)-buffered saline (HBS, 20 mM HEPES, 150 mM NaCl, pH 7.4), containing either 2 mM $CaCl_2$, or 10 mM disodium ethylenediaminetetraacetic (EDTA) as loading and elution buffers, respectively. The purified protein (GST-C2Am) was finally concentrated using 10 kDa concentrators (Vivaspin™, Vivascience, Edgewood, N.Y., USA) and buffer exchanged into HBS. This bacterial expression system consistently yielded ca. 60-80 mg of recombinant GST-C2Am per liter of culture medium. The GST tag was removed from the fusion protein (at a protein concentration of approx. 10 mg mL$^{-1}$) by incubation in HBS, with 2 NIH units of thrombin (GE Healthcare) per milligram of GST-C2Am, for 16 hours at 22° C. The enzyme digest was filtered through 0.22-μm low protein binding filters and the cleaved GST tag removed using a HiPrep™ SP FF column (GE Healthcare), which specifically binds C2Am. The extent of purification was analyzed using SDS-PAGE using pre-cast NUPAGE™ 4-12% gradient gels, sample buffer, molecular weight markers and Novex™ gel tank from Invitrogen (Grand Island, N.Y., USA).

Estimation of Protein Concentration

The concentrations of the unmodified and modified proteins were estimated using a Non-Interfering Protein Assay™ kit (NIPA) (Merck Chemicals Ltd), which is based on the specific binding of copper ions to the peptide backbone. To determine the concentration of Annexin V in the commercially available Annexin V-Alexa Fluor647™ (which also contains 0.1% BSA), the sample was analysed by SDS-PAGE. A corresponding gel was also checked for fluorescence using a Typhoon fluorescence gel scanner (GE Healthcare) using an excitation wavelength of 633 nm. The protein band corresponding to the molecular weight of Annexin V on the SDS-PAGE was confirmed as the only band to fluoresce. The band was then quantified using densitometry, which gives the intensity of the band of interest as a percentage of all the other bands by measuring the optical density. Densitometry and a NIPA assay of the sample, which gave an indication of the total protein concentration, were used to calculate the approximate concentration of Annexin V.

Production of Fluorescently Labeled Protein

The mutant protein (C2Am) was covalently labeled with the fluorochrome Alexa Fluor 647 (AlxAF647), via a reaction between the cysteine-78 residue with the maleimide group of Alexa Fluor 647 C2 maleimide (Invitrogen). Briefly, the protein was reduced using 10 mM DTT for half an hour at room temperature. The protein was then washed in a 5-KDa vivaspin concentrator (Sartorius, Epsom, UK) in HNE buffer (20 mM HEPES, 100 mM NaCl, 5 mM EDTA, pH 7.4). This removed any residual DTT, which interferes with the conjugation reaction. The protein was kept at a concentration in the range 50-100 μM, and approximately a 10-fold molar excess of the fluorescent maleimide dye was added. The reaction was allowed to proceed on a magnetic stirrer at 4° C. overnight. Gel filtration was used to separate the modified protein from unreacted dye. Electrospray ionisation (ESI) mass spectrometry was used to confirm successful modification of the protein, which yielded a single species of approximately 17204 Da (C2Am-AlxAF647). ESI mass spectrometry of Annexin V-Alexa Fluor647™ was also performed. Briefly, samples were desalted using Millipore mC18 Ziptips and eluted with 50% MeCN/0.2% formic acid. Samples were analyzed by direct infusion at a flow rate of 1.7 ml min$^{-1}$ into a Waters QtofMicro, using 70% MeOH/0.2% formic acid as the mobile phase. Typical settings: capillary 3000V, cone 90V, capillary temperature 80° C., desolvation temperature 150° C., calibration by myoglobin and/or trypsinogen collected later in the same file. Deconvolution was conducted using Waters MassLynx MaxEnt 1 software (Waters Ltd, Manchester, UK).

Demonstration of Apoptotic Cell-Binding using Flow Cytometry

The mutant protein (C2Am) was labelled with the fluorochrome Alexa fluor 488-maleimide (AlxF, Invitrogen), via the cysteine-217 residue, in order to produce a fluorescently-labelled apoptosis detection probe (C2Am-AlxF) as described above.

Figure 1:
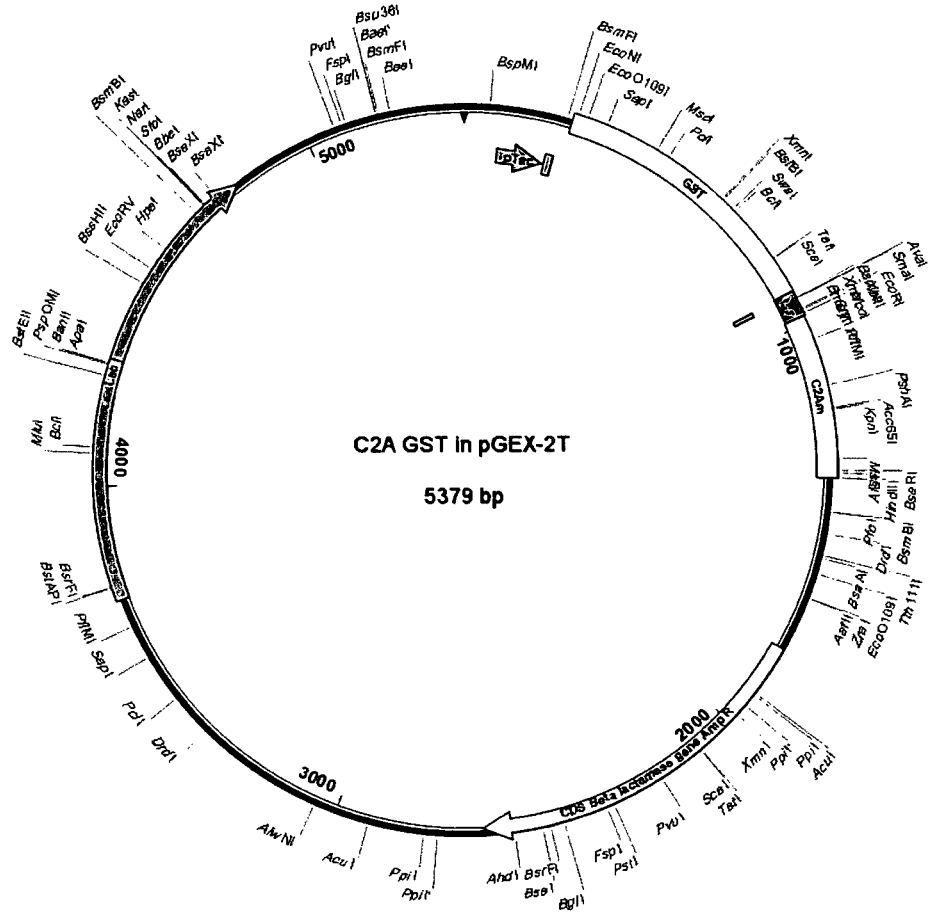
FIG. 1 shows a vector map showing plasmid restriction sites (A) in the expression vector (pGEX-2T, GE Healthcare), showing the glutathione-S-transferase (GST) domain (in cyan), and with the insertion of the linker (in dark green) and C2Am (in yellow).
Figure 2:
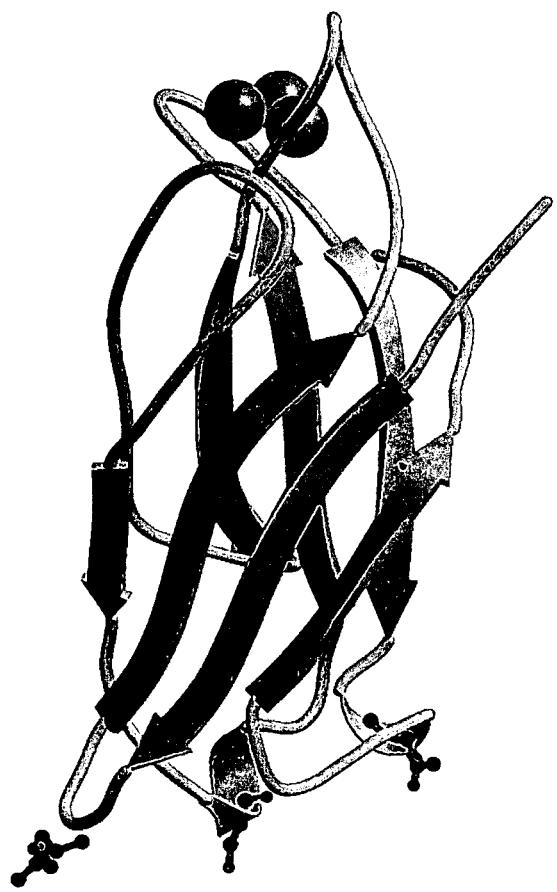
FIG. 2 show a schematic representation of the structure of the C2A domain of synaptotagmin I (from *Rattus norvegicus*) showing the location of the three original candidate mutations left to right: Gln154, Ser217 and Asn248).
Figure 3:
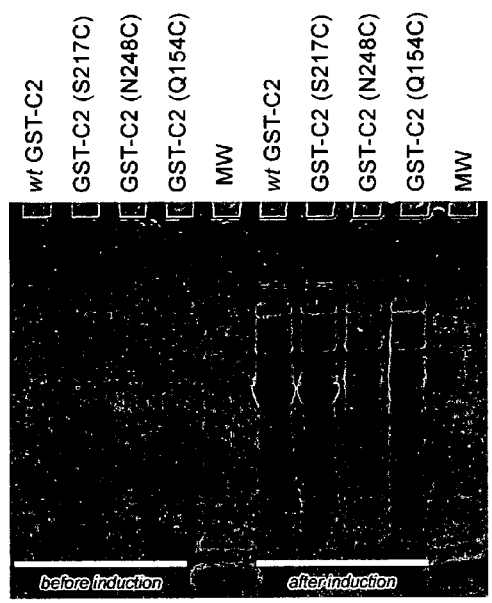
FIG. 3 shows SDS PAGE gels of the three original candidate GST-C2A mutants (S217C, N248C and Q154C), before and after induction with IPTG. The gels show that all transformed bacteria over express the mutant proteins to some degree, but clearly indicates a higher over-expression of S217C.
Figure 4:
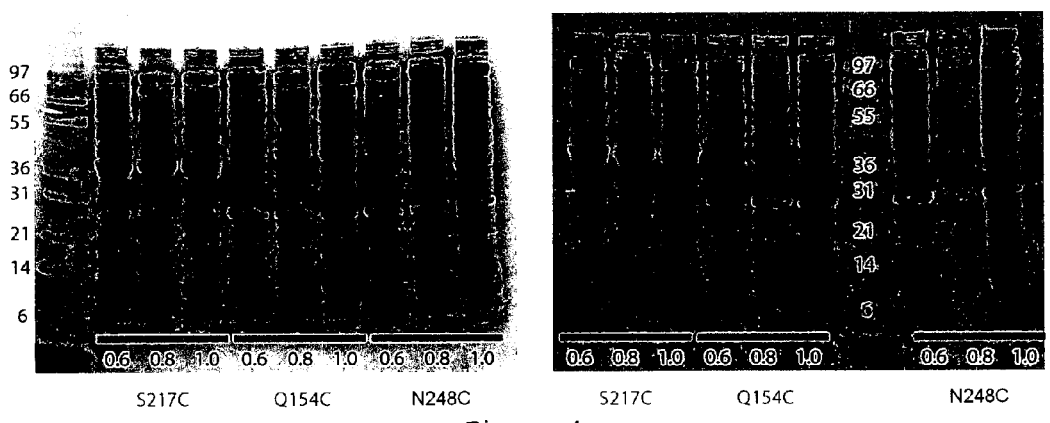
FIG. 4 shows SDS PAGE gels of the three original candidate GST-C2A mutants (2 clones per mutant), showing over-expression yields at different induction ODs (0.6, 0.8, 1.0).
Figure 5:
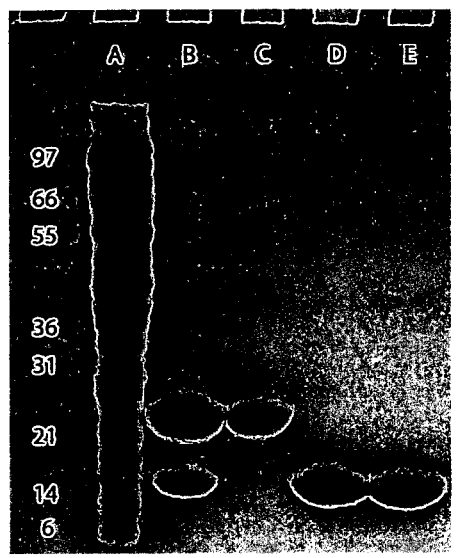
FIG. 5 shows SDS PAGE of GST-C2A purification. Lane (A): non-bound fraction of lysed cells on a GST column, (B): GST and C2A after thrombin cleavage of GST-C2A, (C): non-bound fraction of the HiTrap sepharose column, (D) Eluted C2Am from HiTrap sepharose column, (E) wild-type C2A.
Figure 6:
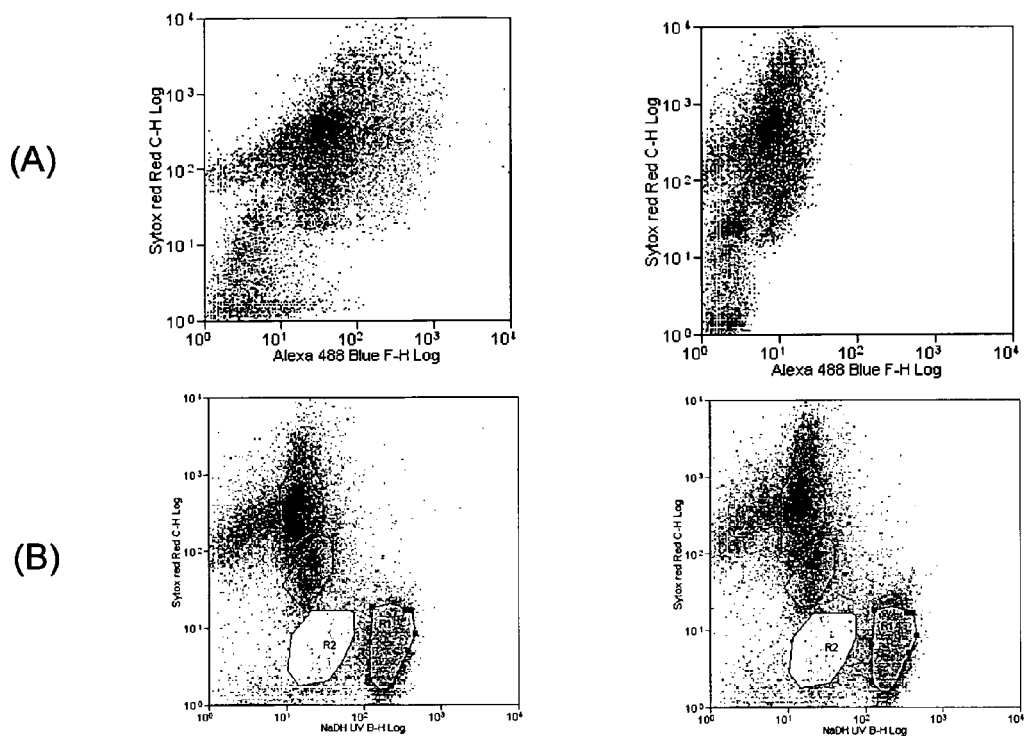
FIG. 6 shows dual scatter plots of EL4 cells labelled with C2Am-AlxF (1$^{st}$ column) or annexinV-AlxF (AnxV-AlxF) (2$^{nd}$ column) (AlxF=Alexa Fluor 488, Invitrogen). (A) Plots of SYTOX™ Red fluorescence (cell death marker; Exc, $\lambda$=633 nm; Em, $\lambda$=670 nm) versus C2Am-AlxF or AnxV-AlxF (Exc, $\lambda$=488 nm; Em, $\lambda$=519 nm). (B) Plots of SYTOX™ Red fluorescence versus UV autofluorescence (The apoptotic cell population (in yellow) presents low UV autofluorescence; this phenomenon may be the result of poly (ADP-ribose) polymerase (PARP)-mediated depletion of the NAD(H) pool in the cell) C2Am-AlxF and AnxV-AlxF used at 0.2 μM. R1 (green)=viable cells; R2 (yellow)=early apoptotic cells; R3 (orange)=late apoptotic cells; R4 (red)=necrotic cells.

Murine lymphoma EL4 cells were treated for 14 hours with a chemotherapeutic drug (etoposide, 15 μM) to induce apoptosis. 10$^6$ cells per sample, resuspended in 100 μL of ice-cold cell-labelling buffer (20 mM HEPES, 150 mM NaCl, 2 mM CaCl$_2$, pH 7.4), were incubated with SYTOX™ Red (Invitrogen; 1.5 μL per sample) and either C2Am-Alx (at 0.2, 0.5 or 2 μM) or AnnexinV-AlexaFluor488 (AnxV-AlxF; at 0.1 or 0.2 μM), for 15 min at room temperature. Samples were then diluted to 1000 μL with cell-labelling buffer. Results are shown in FIG. 6. An increase in fluorescence intensity at 488 nm was observed in early (yellow) and late (orange) apoptotic and necrotic (red) cells. This shift was more pronounced (see FIG. 6A) using C2Am-AlxF than AnxV-AlxF, at the same concentration (0.2 μM).

Figure 7:
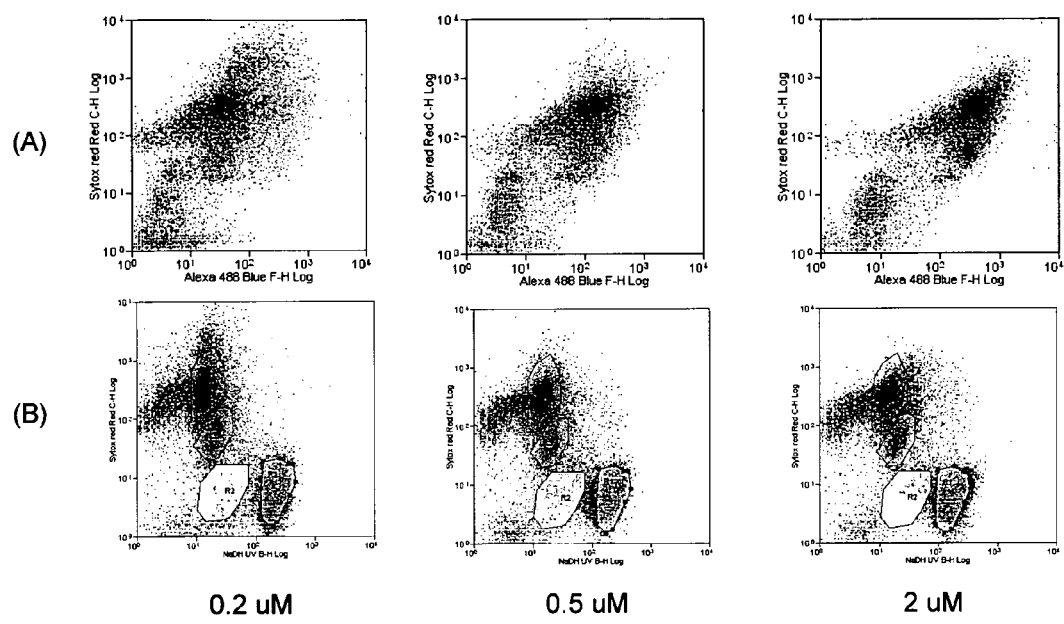
FIG. 7 shows dual scatter plots of EL4 cells labelled with C2Am-AlxF. (A) Plots of SYTOX™ Red fluorescence (cell death marker; Exc, $\lambda$=633 nm; Em, $\lambda$=670 nm) versus C2Am-AlxF (Exc, $\lambda$=488 nm; Em, $\lambda$=519 nm). (B) Plots of SYTOX™ Red fluorescence versus UV autofluorescence. C2Am-AlxF used at 0.2, 0.5 or 2 μM. R1 (green)=viable cells; R2 (yellow)=early apoptotic cells; R3 (orange)=late apoptotic cells; R4 (red)=necrotic cells.

An increase in fluorescence intensity at 488 nm was observed with the increase in probe concentration (FIG. 7). This increased labelling was predominantly seen in early and late apoptotic and necrotic cells.

For the concentration series studies, cell pellets (10$^6$ cells) were washed in ice-cold HEPES-buffered saline (10 mM HEPES, 140 mM NaCl, 2.5 mM CaCl$_2$, pH 7.4) with 1% Fetal calf serum and resuspended in 100 μL of the same buffer containing C2m-AF647 or Annexin V-Alexa Fluor 647™ (Invitrogen), which was used in the range of 0.05 to 1.0 μM total protein concentration, in combination with SYTOX® Green (Invitrogen; 50 nM), prior to incubation for 15 minutes at 37° C. The resulting mixture was washed twice, kept briefly on ice and then analyzed in an LSRII cytometer (BD Biosciences, Rockville, Md. USA), with 20000 cells counted per event. For the time course data, EL4 cells were collected every 2 hours from the point of treatment induction and processed and analyzed following the protocol outlined above. The proteins were used at a fixed concentration of 0.2 μM and 4 nM for C2Am and AnxV, respectively, at each time point. Samples were analyzed in triplicate. For studies of the calcium-dependency of probe binding, the proteins were used at fixed concentrations of 0.1 μM and 2 nM for C2m and AnxV, respectively, in HEPES-buffered saline. For some experiments the Ca$^{2+}$ in the buffer was replaced with 10 mM EDTA. The washes following incubation were also performed in the same buffers.

For the detection of active caspases, treated and untreated EL4 cells were washed and then incubated with green Poly Caspases FLICA® for 30 minutes at 37° C. (300-fold diluted stock). A further wash step was performed before incubating with C2Am and AnxV. The same washing steps were applied as in all the other flow cytometry studies.

Human breast cancer carcinoma cells (MDA-MB-175) were treated for 96 hours with a chemotherapeutic drug (doxorubicin, 1 μg/mL) to induce apoptosis. 10$^6$ cells per sample, trypsinised from 6-well plates (0.25% trypsin, 1 mM EDTA), were resuspended in 100 μL of ice-cold cell-labelling buffer (20 mM HEPES, 150 mM NaCl, 2 mM CaCl$_2$, pH 7.4), containing SYTOX™ Green (Invitrogen; 50 nM) and either C2Am-AF647 (0.2 μM) or AnxV-AF647 (0.004 μM), and incubated for 20 min at 37 C. Samples were then diluted to 1000 μL with cell-labelling buffer before flow cytometric analysis. Results are shown in FIG. 19. An increase in fluorescence intensity at 647 nm was observed in apoptotic (yellow) and necrotic (red) cells versus viable cells (blue), using C2Am-AF647 (FIG. 19C). AnxV-AF647 also labelled apoptotic and necrotic cells more than viable cells, but after 96 h of drug treatment, there was almost no difference in MFI of apoptotic and viable cells stained with AnxV-AF647 (FIG. 19B).

Surface Plasmon Resonance Analysis

Large multilamellar vesicles (LMVs) were prepared using three types of phospholipids (Phosphatidylserine, PS; Phosphatidylethanolamine, PE and Phosphatidylcholine, PC, Avanti Polar Lipids, Alabaster, Ala., USA). A sample of 2.6 μmol of phospholipids (PS:PE:PC mixture in chloroform; molar ratio 35:50:15) was dried under a gentle stream of nitrogen for half an hour and resuspended in 2.6 mL of C2A binding buffer (HBS=20 mM HEPES, 150 mM NaCl, pH 7.4, containing 2 mM $CaCl_2$), by vigorous vortex mixing. This resulted in the formation of a turbid suspension of LMVs, which was then sonicated on ice (3 cycles, 30-s pulses, 10 s intervals between pulses, low power in a Ultrasonic Processor XL Sonicator, from Misonix Inc, Farmingdale, N.Y., USA), until full clarification, indicative of the formation of small unilamellar vesicles (SUVs).

Surface Plasmon Resonance (SPR) analysis was performed on L1 sensor chips using a Biacore T100 system (Biacore, GE Healthcare).

In some experiments, the chip flow cells were washed with a 2-min pulse of a mixture of isopropanol/NaOH 50 mM (2:3 volume) at 5 μL, $min^{-1}$, and one coated with 5 μL of a suspension of SMVs containing 1 mM of phospholipids (at 1 μL $min^{-1}$), generating an average relative response of ca. 2,000 RU (relative units). Unbound multilamellar material was removed from the chip after SMV injection, by applying three 20s regeneration pulses of sodium hydroxide (50 mM, at 20 μL $min^{-1}$).

In other experiments, the chip flow cells were washed with two, 30 s pulses of 20 mM, 3-[(3Cholamidopropyl)dimethylammonio]-1-propanesulfonate (CHAPS, at 30 μL min−1), then one flow cell (test) was coated with a suspension of test SMVs (PS:PE:PC) containing 1 mM of phospholipids (at 5 μL min−1), until an average relative response of ca. 5000 RU (relative units) was reached. Unbound multilamellar material was removed from the lipid bilayer after SMV injection, by applying two, 30 s pulses of sodium hydroxide (50 mM, at 30 μL min−1).

Another flow cell was left uncoated as a control path. In some experiments, another flow cell (control) was coated with a suspension of control SMVs (PE:PC) containing 1 mM of phospholipids (at 5 μL min−1), until an average relative response of ca. 5000 RU (relative units). Control SMVs were prepared using PE and PC (molar ratio 77:23), and unbound material removed as above After a stable baseline had been achieved, the proteins were allowed to interact sequentially with the chip surface of the two flow cells of interest, for 2 min (association phase) and 1 min (dissociation phase) at 30 μL $min^{-1}$ or for 60 s (association phase) at 40 μL $min^{-1}$ at 37° C. The phospholipid bilayer was regenerated using a 15 s or 20 s pulse of HBS containing 10 mM NaEDTA, or (HBS, 20 mm EDTA, pH 7.4) at 40 μL $min^{-1}$, after each individual injection.

Figure 8:
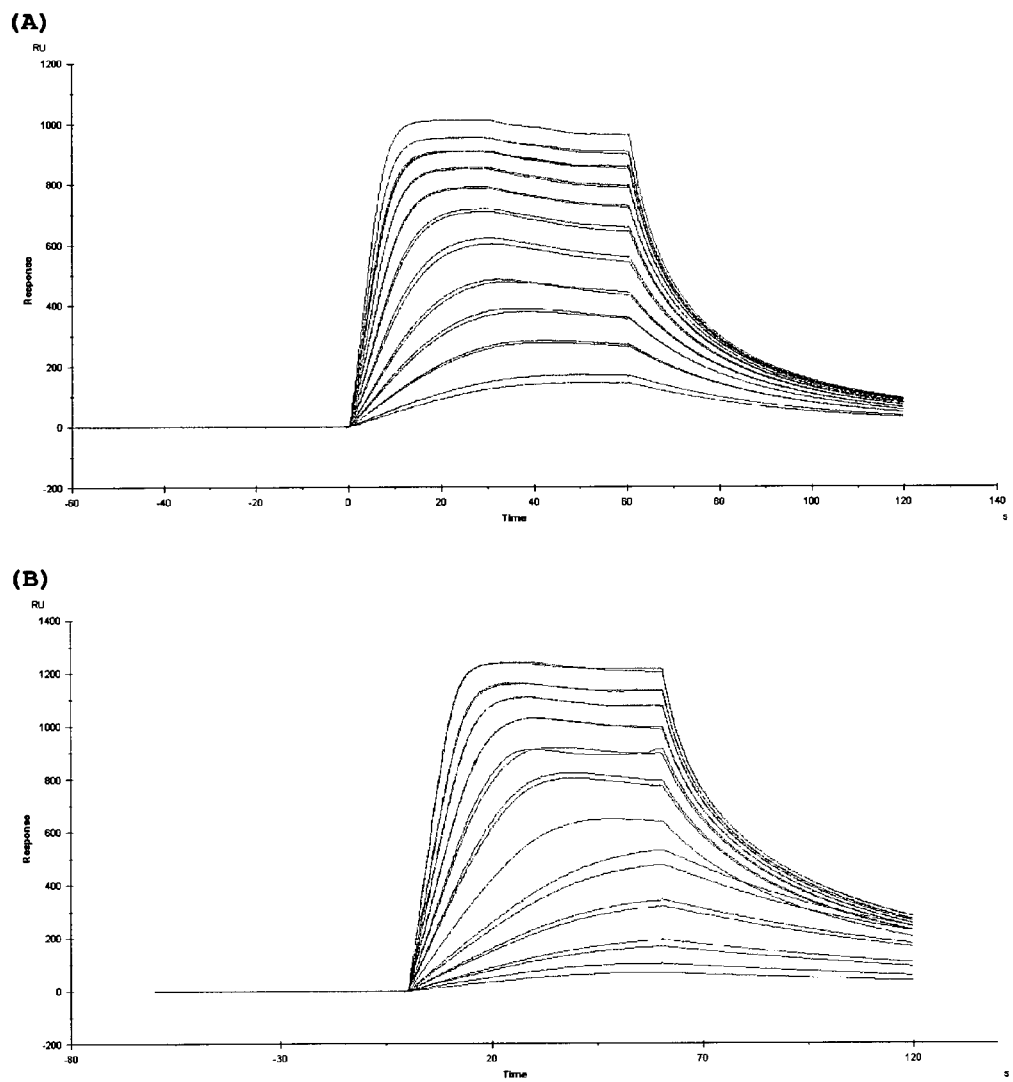
FIG. 8 shows surface plasmon resonance (SPR) sensor-grams for the interaction of wild-type C2A (A) and C2Am (B) with a phosphatidylserine-coated chip. SPR response in arbitrary units. Time in seconds. Duplicate curves. Protein concentration series: 95, 80, 70, 60, 50, 40, 30, 20, 15, 10, 5 nM. Thermal equilibrium data derived from SPR sensorgrams for the binding of wild-type C2A (A) and C2Am (B) to phosphatidylserine was used. SPR response in arbitrary units. The lines correspond to fitting to a 1:1 Langmuir binding model.
Figure 9:
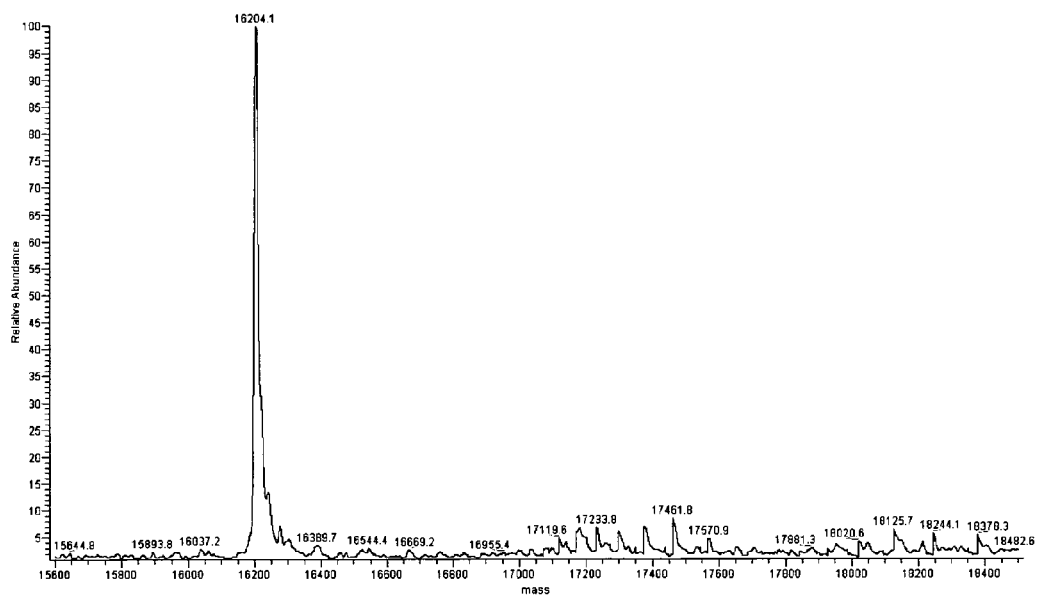
Figure 10:
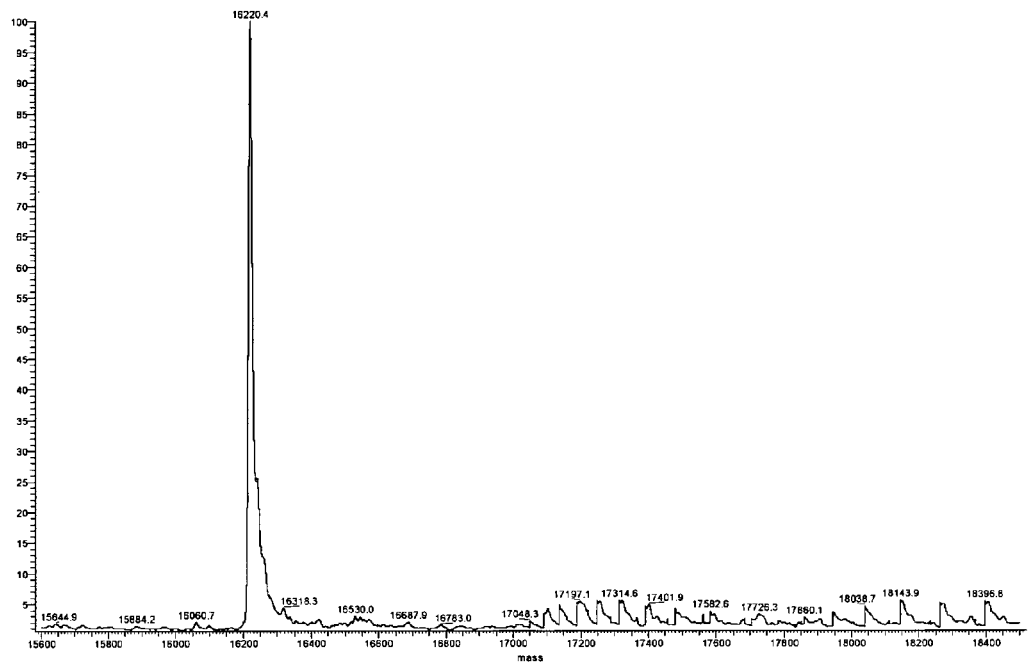
Figure 11:
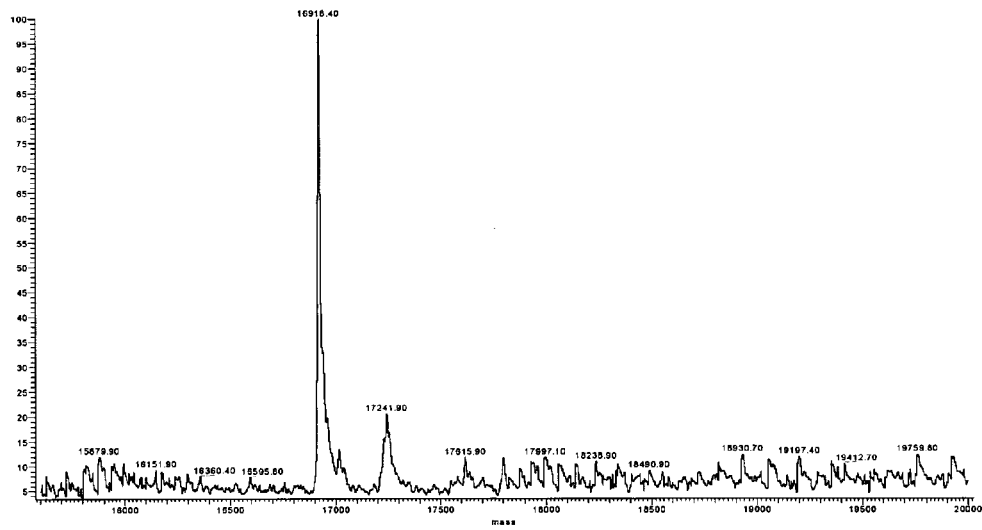

Each protein solution was prepared automatically by the system at varying concentrations from 0 to 100 nM or from 5 nM to 75 nM using automated mix fraction preparation, and all injections were conducted in duplicate in C2A binding buffer at a flow rate of 30 μL $min^{-1}$ and 37° C. All concentrations were analyzed in duplicate. Protein affinity for PS was evaluated by estimating the thermal equilibrium affinity dissociation constants ($K_D$), obtained from the response values 4 s before the end of the association phase of the corresponding interaction sensorgrams (FIG. 8). Double-referencing analysis and the Biacore T100 Evaluation software, version 1.1.1 (BIAcore AB, GE Healthcare) were used.

Cell Culture

EL4 murine lymphoma and MDA-MB-175 human breast carcinoma cells were propagated in RPMI 1640 media, supplemented with 10% fetal calf serum and 2 mM L-glutamine. Cells were sub-cultured in at 37° C. in a humidified atmosphere containing 5% $CO_2$. Cell number and viability were monitored using trypan blue dye staining. EL4 cell death was induced by addition of 5 μM etoposide for 16 hours and MDA-MB-175 cell death was induced by addition of 1 μg/mL of doxorubicin for up to 96 hours.

C2Am-based Probes for Fluorescence Imaging

The mutant protein (C2Am) was labelled with the fluorochrome Alexa fluor 488-maleimide (AlxF, Invitrogen), via the cysteine-217 residue, in order to produce a fluorescently-labelled apoptosis detection probe (C2Am-AlxF). Commercial annexinV was also labelled for comparison, using a similar protocol. Mass spectrometry (electron spray ionization, or ESI) was used to characterise C2Am and C2Am-AlxF.

Briefly, both proteins were kept at concentrations in the range 1-100 μM, and the fluorescent maleimide dye at a concentration in the range 1-10 mM. 0.25 mg Alexa fluor maleimide 488 nm (Invitrogen) was dissolved in 50 μL milliQ water. 20 μg of Anx-V dissolved in 500 μL HBS (HEPES-buffered saline: 20 mM HEPES=4-(2-hydroxyethyl)-1-piperazineethanesulfonic acid, 150 mM NaCl, 1 mM $CaCl_2$, pH 7.4) (1 μM). 0.56 mg of C2Am dissolved in 500 uL HBS (69 μM). 0.5M stock solution of DTT made in milliQ water. 10 mM DTT was added to the proteins and left on magnetic stirrer for 30 minutes at RT. Proteins were then washed in 5-KDa vivaspin concentrator, 3 times in HNE buffer (20 mM HEPES, 100 mM NaCl, 5 mM EDTA, pH 7.4). This removes any residual DTT, which interferes with the conjugation reaction. Once spun down to 0.5 ml, proteins were transferred to 7-mL bijoux flasks. Approximately a 10-fold molar excess of the dye was added to protein (2.9 ul of dye stock to Anx-V and 47.1 μl to the C2Am). Both bijoux kept in the dark. The reaction was allowed to proceed on a magnetic stirrer at 4° C. overnight. Proteins were then washed thoroughly 4 times with HBS in 5 KDa vivaspins. Final working solutions were 28 μM for C2Am-AlxF (1.1 ml) and 0.83 μM for AnxV-AlxF (0.6 ml).

The results of mass spectrometry are shown in FIGS. 9 to 12.

C2Am-based Probes for PET and SPECT.

C2Am was modified with the bifunctional chelate (BFC) Maleimido-mono-amide-DOTA (Macrocyclics) via the cysteine-217 residue in order to produce the $^{111}$Indium labelled apoptosis detection probe (C2Am-DOTA-$^{111}$In) for use in SPECT imaging.

Briefly, 5 mg of C2Am was dissolved in 2 mL HBS (154 μM). A 0.5 M stock solution of DTT was made in milliQ water. 10 mM DTT was added to the protein and left on a magnetic stirrer for 30 minutes at RT. The protein was washed in 5 KDa vivaspin concentrator three times using HNE buffer to remove residual DTT (Dithiothreitol). Once spun down, the protein was resuspended in 1800 μL of HNE buffer and transferred to a 7 mL bijou flask. A 10 fold molar excess of the BFC was dissolved in 200 μL DMSO and added to the protein. The reaction was allowed to proceed at pH 7.4 on a magnetic stirrer at 4° C. overnight. The protein was then washed thoroughly with HBS in 5 KDa vivaspins to remove any residual BFC. The sample was analysed by Electrospray ionisation mass spectrometry for confirmation of successful conjugation. Sample homogeneity was confirmed by mass spectrometry (ESI; see FIG. 11).

The resulting conjugate material may be radiolabelled with $^{111}$In and validated in vitro (cell binding assays) and in vivo on suitable tumour models. SPECT imaging of the C2Am-DOTA-$^{111}$In binding to treated and untreated EL4 tumours may be compared.

Following a similar approach, C2Am may be modified with BFCs and radiolabelled with positron emitting radioisotopes for PET imaging of cell death.

RESULTS

Preparation of C2(S78C).

The serine residue at position 78 of the C2A domain of synaptotagmin I (position 217 of Synaptotagmin I), was replaced by a cysteine residue, using site-directed mutagenesis. Three candidate amino acid residues were selected for replacement: Ser217, Gln154, Asn248. SDS PAGE of the three GST-C2A mutants (S217C, N248C and Q154C) was used to assess the levels of expression before and after IPTG induction. All vector-transformed bacteria expressed the mutant proteins to some degree, but a much higher overexpression was obtained for S217C. The isolated C2 domain [C2(S78C)] was prepared as described above.

Synthesis of C2(S78C)-Alexa Fluor® 647.

C2(S78C) was reacted with a maleimide derivative of Alexa Fluor® 647, as described above. The modified protein (hereafter referred to as C2Am), gave a single peak on electrospray ionization mass spectrometry, with the expected mass of 17204 Da for the modified protein. SDS-PAGE also showed a single band with a mass similar to that expected for the conjugate. Protein modification had little effect on its affinity for PS. Affinity analysis using surface plasmon resonance (SPR) measurements gave similar dissociation constants (Kd) of the two proteins for PS, of 55.4±3.5 nM and 71.0±6.9 nM for the unmodified and modified species respectively. These dissociation constants were corroborated by a kinetic analysis of the SPR data (Table 2).

Detection of Cell Death using Flow Cytometry and C2Am.

The facility of C2Am to detect cell death in a drug-treated murine lymphoma cell line (EL4) using flow cytometry was compared with detection using a commercial preparation of annexin V that had been labeled with the same fluorophore (hereafter refered to as AnxV). Cell death was induced by treatment with etoposide and flow cytometric analysis was performed every two hours for a period of 24 h after drug treatment. Representative scatter plots of cell labeling with Sytox® green (a marker of cell necrosis) versus labelling with C2Am or AnxV, following 16 hours of drug treatment, are shown in FIG. 13. Both agents showed three distinct cell populations (FIGS. 13A and 13B): necrotic (n, x- and y-axis positive), apoptotic (a, x-axis positive and y-axis negative) and viable cells (v, x-axis and y-axis negative). The percentage of the cell population falling into each of these three groups, throughout the time course, is shown for C2Am (FIG. 13D) and for AnxV (FIG. 13E). There was a good correlation between the cell fractions identified by C2Am and AnxV throughout the 24 h following drug treatment (viable, $R^2=0.9956$, apoptotic, $R^2=0.9758$, necrotic, $R^2=0.9957$; n=13).

Treatment of cells with DNA damaging agents, such as etoposide, results in activation of poly ADP-ribose polymerase (PARP) and, since NAD+ is a substrate for PARP, depletion of the cellular NAD(H) pool[13]. As a consequence NADH autofluorescence is decreased considerably upon the induction of cell death using etoposide and this decrease happens relatively early after drug treatment in EL4 cells[14]. Therefore we validated the cell populations identified using C2Am and AnxV by correlating these populations with those identified by a change in NADH UV autofluorescence (FIG. 13C). These correlations are shown in Table 1. In a plot of cell population identified by C2Am or AnxV fluorescence versus cell population identified by NADH autofluorescence, there was a good linear correlation between the viable cell population identified by both proteins and that identified by its high NADH autofluorescence ($R^2=0.996$ and $R^2=0.999$, respectively for AnxV and C2Am), and between the necrotic cell population identified by both proteins and that identified by its low NADH autofluorescence ($R^2=0.998$ and $R^2=0.999$, respectively for AnxV and C2Am). However, AnxV slightly underestimated the fraction of viable cells (slope=0.942, versus a slope=0.994 for C2Am) and markedly underestimated the fraction of apoptotic cells (slope=0.727, versus a slope=0.884 of C2Am), although it showed a slightly better correlation with NAD(H) levels than C2Am ($R^2=0.994$ and $R^2=0.975$, respectively for AnxV and C2Am).

The extent of labelling of each cell population by the two proteins was also analyzed (FIG. 14); where these cell populations had been identified independently from their high NADH autofluorescence (viable cells), low NADH autofluorescence (apoptotic cells) and low NADH autofluorescence and high Sytox® green binding (necrotic cells). Viable cells (FIG. 14A) showed consistently higher staining with AnxV (~4-fold; P<0.0001) compared with C2Am, despite having been used at a 50-fold lower concentration (4 nM AnxV and 200 nM C2Am). Necrotic cells (FIG. 14B) also showed significantly more labelling with AnxV during the first 6 hours after drug treatment (P<0.0001), but not thereafter, and the labelling of apoptotic cells by C2Am was higher (FIG. 14C, P<0.001) for most of the time course. The levels of staining of necrotic cells were similar for both proteins over most of the time course following drug treatment and considerably higher (~10-fold) than those of viable cells.

As a measure of the specificity of the agents for dying versus viable cells, the necrotic/viable (FIG. 14D) and apoptotic/viable (FIG. 14E) ratios were also calculated throughout the time course following drug treatment. C2Am showed greater specificity for apoptotic cells (P<0.01), where the ratio was ~5-fold higher, and necrotic cells (P<0.01), where the ratio was ~3-fold higher than for AnxV.

We have also assessed the facility of C2Am to detect cell death in a drug-treated human breast cancer carcinoma cell line (MDA-MB-231) using flow cytometry, and compared it with detection using AnxV. Cell death was induced by treatment with doxorubicin and flow cytometric analysis was performed every 24 h hours for a period of 96 h after drug treatment. Representative scatter plots of cell labeling with Sytox® green (a marker of cell necrosis) versus labelling with C2Am (C) or AnxV (B), following 48, 72 and 96 hours of drug treatment, are shown in FIG. 19. Both agents showed three distinct cell populations, which have been identified in dual-scatter plots of Sytox Green versus NAD(H) autofluorescence (FIG. 19A): necrotic (red), apoptotic (yellow) and viable cells (blue). C2Am provided a clear separation of the three cell populations (viable, apoptotic and necrotic) throughout the time course of treatment (FIG. 19C). Unlike C2Am, AnxV was less able to distinguish the three populations (FIG. 19C). This was particularly evident 72 hours after treatment induction. As a measure of the specificity of the agents for dying versus viable MDA cells, the apoptotic/viable (FIG. 19D) and necrotic/viable (FIG. 19E) ratios were also calculated throughout the time course following drug treatment. C2Am showed greater specificity for apoptotic cells, where the ratio was ~2-fold higher, and necrotic cells, where the ratio was ~6-fold higher than for AnxV.

Comparison of Cell Labelling with C2A and AnxV with Caspase Activation.

As a further independent measure of cell death we assessed caspase activation using a Poly Caspases FLICA® (Fluorescent-Labeled Inhibitor of CAspases) kit, which is based on caspase inhibitors that are linked to a green (carboxyfluorescein) fluorophore. FLICA is cell-permeant and binds only to active caspases within the cells. Caspase activation is a relatively early event in etoposide-induced cell death in this cell line[14]. Dual scatter plots of treated and untreated cells stained with FLICA and either C2Am or AnxV are shown in FIG. 15. Apoptotic and necrotic cells, in either the untreated or treated cells, were stained by up to 2-fold and 16-fold more, respectively, with FLICA, when compared with viable cells. These plots confirm that that both C2Am and AnxV show low levels of binding to viable cells, which are FLICA negative, but that AnxV binding to these cells is greater than that of C2Am.

Imaging of Dying Cells Stained with C2Am.

Images were acquired from drug-treated cells that had been sorted according to the level of binding of C2Am. Bright field images and the corresponding fluorescence images are shown in FIG. 16. Cells that did not stain with C2Am (A), and consequently showed no fluorescence, had a viable, rounded morphology and an intact membrane in the bright field image. In contrast, cells that stained with C2Am (B), and consequently fluoresced, appeared irregular and with blebbing of the cell membranes in the corresponding bright field image.

Effects of Probe Concentration on Selectivity and Specificity

The concentration ranges studied were between 0.05-1.0 µM and 1-20 nM, respectively for C2Am and AnxV. Since the probe concentration was changing, we gated the three cell populations using NAD(H) autofluorescence. The mean fluorescence intensity (MFI) of viable cells stained by AnxV was considerably higher than for those stained with C2Am (FIG. 17A). The levels of AnxV staining were consistently higher than C2Am for all cell populations (FIG. 17A-C). However, the ratios of apoptotic/viable (FIG. 17E) and necrotic/viable (FIG. 17D) cell staining were higher for C2Am, indicating more specific labelling of both apoptotic ($P<0.05$; [C2Am] ≤0.5 µM, [AnxV]≤0.01 nM) and necrotic cells ($P<0.05$, at [C2Am]=0.1 µM, [AnxV]=2 nM).

$Ca^{2+}$-dependence of C2Am and AnxV Binding to Dying Cells

Binding of C2Am and AnxV to the PS exposed on dying cells is calcium-dependent. However, both proteins are also known to bind other plasma membrane phospholipids in a $Ca^{2+}$-independent manner[15]. Drug-treated cells were incubated in the presence of $Ca^{2+}$ (2 mM) or EDTA (10 mM) and binding of C2Am and AnxV assessed by flow cytometry. The mean fluorescence intensity ratios for binding to apoptotic versus viable and necrotic versus viable cells are shown in FIG. 18. Binding to apoptotic cells was largely $Ca^{2+}$-dependent for both proteins. The residual level of binding in the absence of $Ca^{2+}$ was 4.4% and 12.4% for C2Am and AnxV, respectively. C2Am, however, showed a more pronounced $Ca^{2+}$-independent binding to necrotic cells (52.4% versus 16.1% for AnxV).

The above study evaluates a novel molecular probe for cell death detection based on the C2A domain of synaptotagmin I[7,19], in comparison with AnxV[16], which is a commonly used probe for detecting apoptotic cell death in vitro and in vivo[17,18]. A site-directed mutant of C2A, containing a single cysteine residue C2(S78C), was labelled stoichiometrically with a fluorophore to yield a single chemical species (C2Am). C2Am is shown to detect PS on apoptotic and necrotic murine lymphoma cells. Although less sensitive than a similarly labelled AnxV derivative, C2Am showed lower binding to viable cells and consequently displayed better specificity for the detection of apoptosis and necrosis.

Treatment of a murine lymphoma cell line (EL4) with a chemotherapeutic drug that is used clinically (etoposide, a type II topoisomerase inhibitor) resulted in the induction of apoptosis. The levels of viable, apoptotic and necrotic lymphoma cells detected by C2Am and AnxV were similar and showed a good correlation with the same cell populations determined by their NAD(H) autofluorescence. However, the specificity for apoptotic and necrotic cells, as defined by the apoptotic/viable and necrotic/viable cell ratios respectively, was higher for C2Am than for AnxV. This was largely due to greater binding of AnxV to the viable cell population (see FIGS. 14 and 17). Similar results were obtained for the adherent breast carcinoma human cell line (MDA-MB-231) In order to further investigate the apparent binding of AnxV to viable cells, we used a fluorescently labelled generic inhibitor of activated caspases (FLICA™, Immunochemistry Technologies, LLC), to confirm that this cell population was indeed viable and did not contain cells that might have already entered the apoptotic pathway. Caspase activation is a relatively early event following induction of apoptosis in these cells[14]. This cell population showed 2-fold and 16-fold less labelling with FLICA™, compared with apoptotic and necrotic cells, respectively, and therefore confirmed that this was a genuinely viable cell population. Despite this, it showed considerably more labelling (~5-fold) with AnxV than C2Am.

The chemically well-defined labelled derivative of a site-directed mutant of the C2A domain of synaptotagmin I (S78C) described herein shows lower binding to viable cells than a similarly labelled Annexin V derivative and hence has better specificity for detecting cell death. The lower binding to viable cells may be a consequence of the lower affinity of C2A for PS and may be particularly useful when radionuclide derivatives of this protein are used to detect cell death in vivo since this may reduce the non-specific tissue accumulation that was observed with radionuclide-labelled derivatives of Annexin V.

TABLE 1

|  | Viable | | | | Apoptotic | | | | Necrotic | | | |
| --- | --- | --- | --- | --- | --- | --- | --- | --- | --- | --- | --- | --- |
|  | x | y | $R^2$ | % cells | x | y | $R^2$ | % cells | x | y | $R^2$ | % cells |
| C2Am | 0.9939 | 1.498 | 0.999 | 20-100 | 0.8839 | 0.0361 | 0.9941 | 0-25 | 0.9722 | −1.043 | 0.9988 | 0-70 |
| AnxV | 0.9422 | 4.2731 | 0.9964 | 20-100 | 0.7269 | 3.1232 | 0.9751 | 0-25 | 0.9224 | −1.281 | 0.998 | 0-70 |

TABLE 2

|  | AFFINITY | | KINETICS | | | |
| --- | --- | --- | --- | --- | --- | --- |
|  | KD (nM) | Chi sq | ka (1/Ms) | kd (1/s) | KD (nM) | Chi sq |
| C2Am | 55.4 +/− 3.5 | 5.45 | 2.01E+06 | 0.110 | 54.2 | 26.85 |
| C2Am-AlxAF647 | 71.0 +/− 6.9 | 4.1 | 2.14E+06 | 0.188 | 87.9 | 10.8 |

REFERENCES

1. Dowsett M et al. Endocr Relat Cancer. 1999; 6:25-28.
2. Wheeler J A et al. Int J Radiat Oncol Biol Phys. 1995; 32:1487-1493.
3. Savill J et al Immunol Today. 1993; 14:131-136.
4. Belhocine T, et al. Clin Cancer Res. 2002; 8:2766-2774.
5. Kemerink G J et al. J Nucl Med. 2001; 42:382-387.
6. Boersma H H et al. Br J Radiol. 2003; 76:553-560.
7. Davletov B A et al J Biol Chem. 1993; 268:26386-26390.
8. Sudhof T C et al Cell. 1993; 75:1-4.
9. Krishnan A S et al. Radiology. 2008; 246:854-862.
10. Zhao M, et al. Nat Med. 2001; 7:1241-1244.
11. Zhao M et al. J Nucl Med. 2006; 47:1367-1374.
12. Neves A A et al. Nano Lett. 2007; 7:1419-1423.
13. Sims J L et al Biochemistry. 1983; 22:5188-5194.
14. Witney T H et al. Neoplasia, in press. 2009;
15. Almeida P F et al Biochemistry. 2005; 44:10905-10913.
16. van Genderen H et al. Nat Protoc. 2006; 1:363-367.
17. Petrovsky A et al Cancer Res. 2003; 63:1936-1942.
18. Schellenberger E A et al Neoplasia. 2003; 5:187-192.
19. Sutton R B et al Cell. 1995; 80:929-938.
20. van den Eijnde S M, et al Cytometry. 1997; 29:313-320.
21. Kuo W, J Mol Biol. 2009;
22. Emoto K, et al Exp Cell Res. 1997; 232:430-434.
23. Shao X et al Biochemistry. 1998; 37:16106-16115.
24. Liemann S et al 1997; 53:516-521.
25. Silvestro L et al Biochemistry. 1999; 38:113-121.
26. Concha N O et al Science. 1993; 261:1321-1324.
27. Tait J F et al Arch Biochem Biophys. 1992; 298:187-191.
28. Concha N O et al FEBS Lett. 1992; 314:159-162.
29. Appelt U et al Cell Death Differ. 2005; 12:194-196.

Sequences:

```
EKLGKLQYSL DYDFQNNQLL VGIIQAAELP ALDMGGTSDP YVKVFLLPDK KKKFETKVHR KTLNPVFNEQ

FTFKVPYCEL GGKTLVMAVY DFDRFSKHDI IGEFKVPMNT VDFGHVTEEW RDLQSAEK

SEQ ID NO: 1
Mutated C2A domain of synaptotagmin I.
GAGAAACTGGGAAAGCTCCAATATTCACTGGACTATGACTTCCAGAATAACCAGCTGTTGGTGGGAATCA

TCCAGGCTGCTGAACTGCCCGCCCTGGACATGGGGGGTACATCCGATCCATACGTCAAAGTCTTCCTGCT

GCCTGACAAAAAGAAGAAATTTGAGACTAAAGTCCACCGGAAAACCCTCAATCCAGTCTTCAATGAACAA

TTTACTTTCAAGGTACCCTACTGCGAATTAGGTGGCAAAACCCTGGTGATGGCTGTGTATGACTTTGATC

GCTTCTCCAAGCACGACATCATCGGAGAGTTCAAAGTTCCTATGAACACCGTGGATTTTGGCCATGTGAC

CGAGGAGTGGCGCGATCTCCAGAGCGCTGAGAAA

SEQ ID NO: 2
Mutated C2A domain coding sequence
   1 ACGTTATCGA CTGCACGGTG CACCAATGCT TCTGGCGTCA GGCAGCCATC GGAAGCTGTG

61 GTATGGCTGT GCAGGTCGTA AATCACTGCA TAATTCGTGT CGCTCAAGGC GCACTCCCGT

121 TCTGGATAAT GTTTTTTGCG CCGACATCAT AACGGTTCTG GCAAATATTC TGAAATGAGC

181 TGTTGACAAT TAATCATCGG CTCGTATAAT GTGTGGAATT GTGAGCGGAT AACAATTTCA

241 CACAGGAAAC AGTATTCATG TCCCCTATAC TAGGTTATTG GAAAATTAAG GGCCTTGTGC

301 AACCCACTCG ACTTCTTTTG GAATATCTTG AAGAAAAATA TGAAGAGCAT TTGTATGAGC

361 GCGATGAAGG TGATAAATGG CGAAACAAAA AGTTTGAATT GGGTTTGGAG TTTCCCAATC

421 TTCCTTATTA TATTGATGGT GATGTTAAAT TAACACAGTC TATGGCCATC ATACGTTATA

481 TAGCTGACAA GCACAACATG TTGGGTGGTT GTCCAAAAGA GCGTGCAGAG ATTTCAATGC

541 TTGAAGGAGC GGTTTTGGAT ATTAGATACG GTGTTTCGAG AATTGCATAT AGTAAAGACT

601 TTGAAACTCT CAAAGTTGAT TTTCTTAGCA AGCTACCTGA AATGCTGAAA ATGTTCGAAG

661 ATCGTTTATG TCATAAAACA TATTTAAATG GTGATCATGT AACCCATCCT GACTTCATGT

721 TGTATGACGC TCTTGATGTT GTTTTATACA TGGACCCAAT GTGCCTGGAT GCGTTCCCAA

781 AATTAGTTTG TTTTAAAAAA CGTATTGAAG CTATCCCACA AATTGATAAG TACTTGAAAT

841 CCAGCAAGTA TATAGCATGG CCTTTGCAGG GCTGGCAAGC CACGTTTGGT GGTGGCGACC

901 ATCCTCCAAA ATCGGATCTG GTTCCGCGNG GATCCCCGGG AATTTCCGGT GGTGGTGGTG

961 GAATTCTAGA CTCCATGGTG GAGAAACTGG GAAAGCTCCA ATATTCACTG GACTATGACT

1021 TCCAGAATAA CCAGCTGTTG GTGGGAATCA TCCAGGCTGC TGAACTGCCC GCCCTGGACA

1081 TGGGGGGTAC ATCCGATCCA TACGTCAAAG TCTTCCTGCT GCCTGACAAA AAGAAGAAAT

1141 TTGAGACTAA AGTCCACCGG AAAACCCTCA ATCCAGTCTT CAATGAACAA TTTACTTTCA
```

-continued

```
1201 AGGTACCCTA CTGCGAATTA GGTGGCAAAA CCCTGGTGAT GGCTGTGTAT GACTTTGATC
1261 GCTTCTCCAA GCACGACATC ATCGGAGAGT TCAAAGTTCC TATGAACACC GTGGATTTTG
1321 GCCATGTGAC CGAGGAGTGG CGCGATCTCC AGAGCGCTGA GAAATAAGCT TAATTCATCG
1381 TGACTGACTG ACGATCTGCC TCGCGCGTTT CGGTGATGAC GGTGAAAACC TCTGACACAT
1441 GCAGCTCCCG GAGACGGTCA CAGCTTGTCT GTAAGCGGAT GCCGGGAGCA GACAAGCCCG
1501 TCAGGGCGCG TCAGCGGGTG TTGGCGGGTG TCGGGGCGCA GCCATGACCC AGTCACGTAG
1561 CGATAGCGGA GTGTATAATT CTTGAAGACG AAAGGGCCTC GTGATACGCC TATTTTTATA
1621 GGTTAATGTC ATGATAATAA TGGTTTCTTA GACGTCAGGT GGCACTTTTC GGGGAAATGT
1681 GCGCGGAACC CCTATTTGTT TATTTTTCTA AATACATTCA AATATGTATC CGCTCATGAG
1741 ACAATAACCC TGATAAATGC TTCAATAATA TTGAAAAAGG AAGAGTATGA GTATTCAACA
1801 TTTCCGTGTC GCCCTTATTC CCTTTTTTGC GGCATTTTGC CTTCCTGTTT TTGCTCACCC
1861 AGAAACGCTG GTGAAAGTAA AAGATGCTGA AGATCAGTTG GGTGCACGAG TGGGTTACAT
1921 CGAACTGGAT CTCAACAGCG GTAAGATCCT TGAGAGTTTT CGCCCCGAAG AACGTTTTCC
1981 AATGATGAGC ACTTTTAAAG TTCTGCTATG TGGCGCGGTA TTATCCCGTG TTGACGCCGG
2041 GCAAGAGCAA CTCGGTCGCC GCATACACTA TTCTCAGAAT GACTTGGTTG AGTACTCACC
2101 AGTCACAGAA AAGCATCTTA CGGATGGCAT GACAGTAAGA GAATTATGCA GTGCTGCCAT
2161 AACCATGAGT GATAACACTG CGGCCAACTT ACTTCTGACA ACGATCGGAG GACCGAAGGA
2221 GCTAACCGCT TTTTTGCACA ACATGGGGGA TCATGTAACT CGCCTTGATC GTTGGGAACC
2281 GGAGCTGAAT GAAGCCATAC CAAACGACGA GCGTGACACC ACGATGCCTG CAGCAATGGC
2341 AACAACGTTG CGCAAACTAT TAACTGGCGA ACTACTTACT CTAGCTTCCC GGCAACAATT
2401 AATAGACTGG ATGGAGGCGG ATAAAGTTGC AGGACCACTT CTGCGCTCGG CCCTTCCGGC
2461 TGGCTGGTTT ATTGCTGATA AATCTGGAGC CGGTGAGCGT GGGTCTCGCG GTATCATTGC
2521 AGCACTGGGG CCAGATGGTA AGCCCTCCCG TATCGTAGTT ATCTACACGA CGGGGAGTCA
2581 GGCAACTATG GATGAACGAA ATAGACAGAT CGCTGAGATA GGTGCCTCAC TGATTAAGCA
2641 TTGGTAACTG TCAGACCAAG TTTACTCATA TATACTTTAG ATTGATTTAA AACTTCATTT
2701 TTAATTTAAA AGGATCTAGG TGAAGATCCT TTTTGATAAT CTCATGACCA AAATCCCTTA
2761 ACGTGAGTTT TCGTTCCACT GAGCGTCAGA CCCCGTAGAA AAGATCAAAG GATCTTCTTG
2821 AGATCCTTTT TTTCTGCGCG TAATCTGCTG CTTGCAAACA AAAAAACCAC CGCTACCAGC
2881 GGTGGTTTGT TTGCCGGATC AAGAGCTACC AACTCTTTTT CCGAAGGTAA CTGGCTTCAG
2941 CAGAGCGCAG ATACCAAATA CTGTCCTTCT AGTGTAGCCG TAGTTAGGCC ACCACTTCAA
3001 GAACTCTGTA GCACCGCCTA CATACCTCGC TCTGCTAATC CTGTTACCAG TGGCTGCTGC
3061 CAGTGGCGAT AAGTCGTGTC TTACCGGGTT GGACTCAAGA CGATAGTTAC CGGATAAGGC
3121 GCAGCGGTCG GGCTGAACGG GGGGTTCGTG CACACAGCCC AGCTTGGAGC GAACGACCTA
3181 CACCGAACTG AGATACCTAC AGCGTGAGCT ATGAGAAAGC GCCACGCTTC CCGAAGGGAG
3241 AAAGGCGGAC AGGTATCCGG TAAGCGGCAG GGTCGGAACA GGAGAGCGCA CGAGGGAGCT
3301 TCCAGGGGGA AACGCCTGGT ATCTTTATAG TCCTGTCGGG TTTCGCCACC TCTGACTTGA
3361 GCGTCGATTT TTGTGATGCT CGTCAGGGGG GCGGAGCCTA TGGAAAAACG CCAGCAACGC
3421 GGCCTTTTTA CGGTTCCTGG CCTTTTGCTG GCCTTTTGCT CACATGTTCT TTCCTGCGTT
3421 ATCCCCTGAT TCTGTGGATA ACCGTATTAC CGCCTTTGAG TGAGCTGATA CCGCTCGCCG
3481 CAGCCGAACG ACCGAGCGCA GCGAGTCAGT GAGCGAGGAA GCGGAAGAGC GCCTGATGCG
```

```
3541 GTATTTTCTC CTTACGCATC TGTGCGGTAT TTCACACCGC ATAAATTCCG ACACCATCGA

3601 ATGGTGCAAA ACCTTTCGCG GTATGGCATG ATAGCGCCCG GAAGAGAGTC AATTCAGGGT

3661 GGTGAATGTG AAACCAGTAA CGTTATACGA TGTCGCAGAG TATGCCGGTG TCTCTTATCA

3721 GACCGTTTCC CGCGTGGTGA ACCAGGCCAG CCACGTTTCT GCGAAAACGC GGGAAAAAGT

3781 GGAAGCGGCG ATGGCGGAGC TGAATTACAT TCCCAACCGC GTGGCACAAC AACTGGCGGG

3841 CAAACAGTCG TTGCTGATTG GCGTTGCCAC CTCCAGTCTG GCCCTGCACG CGCCGTCGCA

3901 AATTGTCGCG GCGATTAAAT CTCGCGCCGA TCAACTGGGT GCCAGCGTGG TGGTGTCGAT

3961 GGTAGAACGA AGCGGCGTCG AAGCCTGTAA AGCGGCGGTG CACAATCTTC TCGCGCAACG

4021 CGTCAGTGGG CTGATCATTA ACTATCCGCT GGATGACCAG GATGCCATTG CTGTGGAAGC

4081 TGCCTGCACT AATGTTCCGG CGTTATTTCT TGATGTCTCT GACCAGACAC CCATCAACAG

4141 TATTATTTTC TCCCATGAAG ACGGTACGCG ACTGGGCGTG GAGCATCTGG TCGCATTGGG

4201 TCACCAGCAA ATCGCGCTGT TAGCGGGCCC ATTAAGTTCT GTCTCGGCGC GTCTGCGTCT

4321 GGCTGGCTGG CATAAATATC TCACTCGCAA TCAAATTCAG CCGATAGCGG AACGGGAAGG

4381 CGACTGGAGT GCCATGTCCG GTTTTCAACA AACCATGCAA ATGCTGAATG AGGGCATCGT

4441 TCCCACTGCG ATGCTGGTTG CCAACGATCA GATGGCGCTG GGCGCAATGC GCGCCATTAC

4501 CGAGTCCGGG CTGCGCGTTG GTGCGGATAT CTCGGTAGTG GGATACGACG ATACCGAAGA

4561 CAGCTCATGT TATATCCCGC CGTTAACCAC CATCAAACAG GATTTTCGCC TGCTGGGGCA

4621 AACCAGCGTG GACCGCTTGC TGCAACTCTC TCAGGGCCAG GCGGTGAAGG GCAATCAGCT

4681 GTTGCCCGTC TCACTGGTGA AAGAAAAAC CACCCTGGCG CCCAATACGC AAACCGCCTC

4741 TCCCCGCGCG TTGGCCGATT CATTAATGCA GCTGGCACGA CAGGTTTCCC GACTGGAAAG

4801 CGGGCAGTGA GCGCAACGCA ATTAATGTGA GTTAGCTCAC TCATTAGGCA CCCCAGGCTT

4861 TACACTTTAT GCTTCCGGCT CGTATGTTGT GTGGAATTGT GAGCGGATAA CAATTTCACA

4921 CAGGAAACAG CTATGACCAT GATTACGGAT TCACTGGCCG TCGTTTTACA ACGTCGTGAC

4981 TGGGAAAACC CTGGCGTTAC CCAACTTAAT CGCCTTGCAG CACATCCCCC TTTCGCCAGC

5041 TGGCGTAATA GCGAAGAGGC CCGCACCGAT CGCCCTTCCC AACAGTTGCG CAGCCTGAAT

5101 GGCGAATGGC GCTTTGCCTG GTTTCCGGCA CCAGAAGCGG TGCCGGAAAG CTGGCTGGAG

5161 TGCGATCTTC CTGAGGCCGA TACTGTCGTC GTCCCCTCAA ACTGGCAGAT GCACGGTTAC

5221 GATGCGCCCA TCTACACCAA CGTAACCTAT CCCATTACGG TCAATCCGCC GTTTGTTCCC

5281 ACGGAGAATC CGACGGGTTG TTACTCGCTC ACATTTAATG TTGATGAAAG CTGGCTACAG

5341 GAAGGCCAGA CGCGAATTAT TTTTGATGGC GTTGGAATT
```

SEQ ID NO: 3
pGEX-2T vector with C2A-GST fusion insert.

---

The invention claimed is:

1. An imaging agent comprising;
a synaptotagmin C2A domain polypeptide which binds to phosphatidylserine and comprises the amino acid sequence of SEQ ID NO: 1 and having a detectable label attached to the cysteine residue at position 78 of SEQ ID NO: 1.

2. An imaging agent comprising;
a synaptotagmin C2A domain polypeptide which comprises either i) the amino acid sequence of SEQ ID NO: 1 or ii) an amino acid sequence which differs from SEQ ID NO: 1 by insertion, addition, substitution or deletion of 1 to 10 amino acids and has a cysteine residue at a position corresponding to position 78 of SEQ ID NO: 1; and,
a detectable label attached to the cysteine residue.

3. An imaging agent according to claim 2 wherein the synaptotagmin C2A domain polypeptide comprises the amino acid sequence of SEQ ID NO: 1.

4. An imaging agent according to claim 2 wherein the detectable label is a fluorescent detectable label, a magnetic resonance imaging detectable label or a scintigraphic detectable label.

5. An imaging agent according to claim 4 wherein the magnetic resonance imaging detectable label is a paramagnetic or superparamagnetic ion.

6. An imaging agent according to claim 5 wherein the magnetic resonance imaging detectable label is a gadolinium ($Gd^{3+}$) ion.

7. An imaging agent according to claim 4 wherein the scintigraphic detectable label is a positron emitting radioisotope or a gamma emitting radioisotope.

8. An imaging agent according to claim 7 wherein the gamma emitting radioisotope is Technetium$^{99m}$ or Indium$^{111}$ or wherein the positron emitting radioisotope is Fluorine$^{18}$, Gallium$^{68}$ or Copper$^{64}$.

9. An imaging agent according to claim 2 wherein the detectable label comprises a thiol-reactive group which binds to the cysteine residue of the synaptotagmin C2A domain polypeptide.

10. An imaging agent according to claim 2 further comprising a bifunctional linker, wherein the linker comprises a thiol-reactive group, which binds to the cysteine residue of the synaptotagmin C2A domain polypeptide and a binding moiety which binds to the detectable label.

11. An imaging agent according to claim 10 wherein the detectable label is a metal ion and the binding moiety is a chelate which complexes with the metal ion.

12. An imaging agent according to claim 11 wherein the chelate is DOTA or DTPA.

13. An imaging agent according to claim 9 wherein the thiol-reactive group is a maleimido group.

14. A method of imaging cell death in an individual comprising;
administering an imaging agent according to claim 2 to an individual, and;
producing one or more images of the distribution of the imaging agent within the individual.

15. A method according to claim 14 wherein the individual has one or more sites of cell death, and the one or more images show the distribution of the imaging agent at the one or more sites.

16. A method according to claim 14 wherein the individual has a tumour, and the one or more images show the distribution of the imaging agent at the site of the tumour.

17. A method of determining the effectiveness of a cancer therapy in treating a tumour in an individual comprising;
administering an imaging agent according to claim 2 to an individual before cancer therapy and during or after cancer therapy; and,
producing one or more images of the distribution of the imaging agent at the site of the tumour in the individual,
wherein an increase in binding of the imaging agent at the site of the tumour during or after said therapy relative to before said therapy is indicative that the therapy is effective in the individual.

18. A method of determining the effectiveness of a therapy for a disease condition characterised by one or more sites of cell death in an individual comprising;
administering an imaging agent according to claim 2 to an individual before and during or after therapy; and,
producing one or more images of the distribution of the imaging agent at the one or more sites of cell death in the individual,
wherein a decrease in binding of the imaging agent at one or more sites of cell death during or after said therapy relative to before said therapy is indicative that the therapy is effective in the individual, and
wherein the disease condition is selected from the group consisting of cardiac infarction, cardiac plaque formation, inflammation and infection.

19. A method of preparing a pharmaceutical composition for use in imaging cell death in an individual comprising
providing an imaging agent according to claim 2, and;
admixing the imaging agent with a pharmaceutically acceptable excipient.

20. A kit for imaging of cell death comprising a first container comprising imaging agent according to claim 2; and a second container comprising a pharmaceutically acceptable diluent.

* * * * *

UNITED STATES PATENT AND TRADEMARK OFFICE
CERTIFICATE OF CORRECTION

PATENT NO.       : 8,685,371 B2
APPLICATION NO.  : 12/989310
DATED            : April 1, 2014
INVENTOR(S)      : Brindle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 437 days.

Signed and Sealed this

Twenty-ninth Day of September, 2015

Michelle K. Lee
*Director of the United States Patent and Trademark Office*